United States Patent
Epps, III et al.

(10) Patent No.: US 11,525,024 B2
(45) Date of Patent: Dec. 13, 2022

(54) BIO-BASED POLYMERS FROM RAW LIGNOCELLULOSIC BIOMASS

(71) Applicants: Thomas H. Epps, III, Bear, DE (US); Angela L. Holmberg, Somerville, MA (US); Kaleigh H. Nicastro, Newark, DE (US); Shu Wang, Copley, OH (US); Basudeb Saha, Newark, DE (US); Li Shuai, Blacksburg, VA (US); Dionisios G. Vlachos, Voorhees, NJ (US)

(72) Inventors: Thomas H. Epps, III, Bear, DE (US); Angela L. Holmberg, Somerville, MA (US); Kaleigh H. Nicastro, Newark, DE (US); Shu Wang, Copley, OH (US); Basudeb Saha, Newark, DE (US); Li Shuai, Blacksburg, VA (US); Dionisios G. Vlachos, Voorhees, NJ (US)

(73) Assignee: UNIVERSITY OF DELAWARE, Newark, DE (US)

(*) Notice: Subject to any disclaimer, the term of this patent is extended or adjusted under 35 U.S.C. 154(b) by 0 days.

(21) Appl. No.: 16/243,718

(22) Filed: Jan. 9, 2019

(65) Prior Publication Data
US 2019/0144590 A1 May 16, 2019

Related U.S. Application Data

(63) Continuation-in-part of application No. 15/208,135, filed on Jul. 12, 2016, now Pat. No. 10,253,131.
(Continued)

(51) Int. Cl.
*C08F 220/18* (2006.01)
*C09J 7/38* (2018.01)
(Continued)

(52) U.S. Cl.
CPC ........ *C08F 293/005* (2013.01); *B32B 27/302* (2013.01); *B32B 27/308* (2013.01);
(Continued)

(58) Field of Classification Search
None
See application file for complete search history.

(56) References Cited

U.S. PATENT DOCUMENTS

| | | | |
|---|---|---|---|
| 5,141,790 A | * | 8/1992 | Calhoun ............ C09J 7/38 428/40.4 |
| 5,948,590 A | | 9/1999 | Aoshima |

(Continued)

FOREIGN PATENT DOCUMENTS

| | | | |
|---|---|---|---|
| JP | 10306145 A | | 11/1998 |
| JP | 2002155255 A | * | 5/2002 |
| JP | 2006259558 A | | 9/2006 |

OTHER PUBLICATIONS

Jullian, N. et al., "Structure and rheology of di-and tri block copolymers of polystyrene and poly(n-butyl acrylate)". J. Rheol. 2011, 55 (2), 379-400. (Year: 2011).*

(Continued)

*Primary Examiner* — Richard A Huhn
(74) *Attorney, Agent, or Firm* — RatnerPrestia

(57) ABSTRACT

Disclosed herein is a method of making polymerizable bio-based monomers containing one phenolic hydroxyl group which has been derivatized to provide at least one polymerizable functional group which is an ethylenically unsaturated functional group (such as a [meth]acrylate group), where the precursors of the polymerizable bio-based monomers are derived from raw lignin-containing biomass. Also disclosed herein are bio-based copolymers prepared from such bio-based monomers and a co-monomer, and methods of making and using such bio-based copolymers. In
(Continued)

particular, the bio-based copolymers can be used as pressure sensitive adhesives, binders, and polymer electrolytes.

19 Claims, 7 Drawing Sheets

Related U.S. Application Data

(60) Provisional application No. 62/713,571, filed on Aug. 2, 2018, provisional application No. 62/615,040, filed on Jan. 9, 2018, provisional application No. 62/191,551, filed on Jul. 13, 2015.

(51) Int. Cl.

| | | |
|---|---|---|
| C09J 125/18 | (2006.01) | |
| C09J 133/08 | (2006.01) | |
| C09J 153/00 | (2006.01) | |
| B32B 27/30 | (2006.01) | |
| C08F 293/00 | (2006.01) | |
| C07C 69/618 | (2006.01) | |
| C08G 83/00 | (2006.01) | |
| C09J 9/02 | (2006.01) | |
| H01M 4/62 | (2006.01) | |
| H01M 10/0565 | (2010.01) | |
| C07C 67/14 | (2006.01) | |
| C07C 41/18 | (2006.01) | |
| C07C 41/38 | (2006.01) | |
| C08H 8/00 | (2010.01) | |

(52) U.S. Cl.
CPC .............. *C07C 41/18* (2013.01); *C07C 41/38* (2013.01); *C07C 67/14* (2013.01); *C07C 69/618* (2013.01); *C08G 83/005* (2013.01); *C09J 7/38* (2018.01); *C09J 7/385* (2018.01); *C09J 7/387* (2018.01); *C09J 9/02* (2013.01); *C09J 125/18* (2013.01); *C09J 133/08* (2013.01); *C09J 153/00* (2013.01); *H01M 4/622* (2013.01); *H01M 10/0565* (2013.01); *C08F 220/1806* (2020.02); *C08F 2438/01* (2013.01); *C08G 2170/40* (2013.01); *C08H 8/00* (2013.01); *C09J 2203/33* (2013.01); *C09J 2301/414* (2020.08); *C09J 2400/163* (2013.01); *C09J 2400/226* (2013.01); *C09J 2400/283* (2013.01); *C09J 2433/00* (2013.01); *C09J 2453/00* (2013.01); *C09J 2471/00* (2013.01); *C09J 2497/00* (2013.01); *H01M 2300/0082* (2013.01)

(56) References Cited

U.S. PATENT DOCUMENTS

| | | | |
|---|---|---|---|
| 6,121,398 | A | 9/2000 | Wool et al. |
| 7,524,909 | B2 | 4/2009 | Palmese et al. |
| 10,253,131 | B2 | 4/2019 | Holmberg et al. |
| 2003/0207462 | A1 | 11/2003 | Kitagawa |
| 2007/0269480 | A1 | 11/2007 | Richard et al. |
| 2012/0184521 | A1 | 7/2012 | Kawaminami et al. |
| 2012/0295993 | A1 | 11/2012 | Wool |
| 2013/0131185 | A1 | 5/2013 | Plettner et al. |
| 2013/0337711 | A1 | 12/2013 | Wool |
| 2014/0275435 | A1* | 9/2014 | Holmberg ........... C08F 293/005 525/401 |

OTHER PUBLICATIONS

Technology of Pressure-Sensitive Adhesives and Products. Chapter 3: "Block Copolymer-Based Hot-Melt Pressure-Sensitive Adhesives". Edited by Istvan Benedek, Mikhail M. Feldstein. 1st Edition, 2008, Taylor & Francis. (Year: 2008).*
Altwicker, "The Chemistry of Stable Phenoxy Radicals", Chemical Reviews, vol 67, No. 5, Sep. 25, 1967—pp. 475-531.
AkoNobel Product Data Sheet Perkadox® AIBN. AkzoNobel PalymerChemistry: Amersfoort, The Netherlands, 2015, pp. 1-4.
Barner-Kowollik et al., "The Future of Reversible Addition Fragmentation Chain Transfer Polymerization", Journal of Polymer Science Part A: Polymer Chemistry 2008, 46 (17)—pp. 5715-5723.
Beach et al., "Properties of Thermosets Derived from Chemically Modified Triglycerides and Bio-Based Comonomers", i Applied Science, 2013, vol. 3 - pp. 684-693, i.
Brydson, J., "Plastics Materials", Sixth Edition, 1995—8 pages.
Chung et al., "Chemistry of Lignin-based Materials". Green Materials 2013, 1 (3)—pp. 137-160.
Creton, C., "Pressure-sensitive Adhesives; An Introductory Course", MRS Bulletin 2003, 28 (6)—pp. 434-439.
Gall et al., "Biochemical Transformation of Lignin for Deriving Valued Commodities from Lignocellulose", Current Opinion in Biotechnology, 2017, 45—pp. 120-126.
Gallagher et al., "Acrylic Triblock Copolymers Incorporating Isosorbide for Pressure Sensitive Adhesives", ACS Sustainable Chemistry & Engineering 2016, 4 (6)—pp. 3379-3387.
Gloia et al., "Tunable Thermosetting Epoxies Based on Fractionated and Well-Characterized Lignins" Journal of the American Chemical Society 2018, 140 (11)—pp. 4054-4061.
Glasser et al., "Derivatives of Lignin and Ligninlike Models with Acrylate Functionality", Chapter 41, ACS Symposium Series, 1989—pp. 515-522.
Holmberg et al., "A Facile Method for Generating Designer Block Copolymers from Functionalized Lignin Model Compounds", ACS Sustainable Chemistry & Engineering, 2014—5 pages.
Holmberg et al., "RAFT Polmerization and Associated Reactivity Ratios of Methacrylate-Functionalized Mixed Bio-oil Constituents", Polym. Chem. 2015, 6(31)—pp. 5728-5739.
Holmberg et al., "Softwood Lignin-Based Methacrylate Polymers with Tunable Thermal and Viscoelasatic Properties", Macromolecules, 2016—10 pages.
Holmberg et al., "Syringyl Methacrylate, a Hardware Lignin-Based Monomer for High Tg Polymeric Materials," ACS Macro Lett. 2016, 5—pp. 574-578.
Kharas at al., "Novel Copolymers of Styrene. 3. Oxy Ring-Distributed 2-cyano-3-phenyl-2-propenamides", Journal of Macromolecular Science, Part A: Pure and Applied Chemistry (2013) 50—pp. 575-580.
Lau et al., "Polmerization Behavior of 2,6-dimethoxystyrene", Can. J. Chem., 1969, 47(11), pp. 2057-2060.
Lewis et el., "The Influence of Hydrogen Bonding Side-Groups an Viscoelastic Behavior of Linear and Network Polymers", Macromolecules, 2014, vol. 47—pp. 729-740.
Lewis, C., "Structure Property Relationships for Polymers Bearing Reversibily Associating Side-groups", Doctoral Dissertation University of Rochester, 2014, 237 pages.
Mather, B., "Non-Covalent Interactions in Block Copolymers Synthesized via Living Polymerization Techniques", Doctoral Dissertation, Virginia Tech, 2007—593 pages.
Moad et al., "Living Radical Polymerization by the RAFT Process", Aust. J. Chem., 2005, 58—pp. 379-410.
O'Connor et al., "The Effect of Molecular Weight and Temperature on Tack Properties of Model Polyisobutylenes", International Journal of Adhesion and Adhesives 2004, 24 (4)—pp. 335-346.
Peykova et al., "Adhesive Properties of Acrylate Copolymers: Effect of the Nature of the Substrate and Copolymer Functionality", International Journal of Adhesion and Adhesives 2012, 34—pp. 107-116.
Rojo et al., "The Preparation of High Conversion Polymeric Systems Containing Eugenol Residues and Their Rheological Characterization", Journal of Material Science; Materials in Medicine, 2008, vol. 19,—pp. 1467-1477.
Saha et al., "Substituent Effects in ATRP of Polystyrene Brushes", Polymer Preprints (American Chemical Society, Div. of Polymer Chemistry) 2007, 48(1)—p. 783.

(56) References Cited

OTHER PUBLICATIONS

Schraub et al., "Setective [2+2]—Cycloaddition In Methacrylic Stilbene Polymers without Interference from E/Z-Isomerization", Macromolecules, 2011, 44—pp. 8755-8762.
Shuai et al., "Formaldehyde Stabilization Facilitates Lignin Monomer Production During Biomass Depolymerization", Science 2016, 354 (6310)—pp. 329-333.
Stanzione et al., "Lignin-based Bio-oil Mimic as Biobased Resin for Composite Applications", ACS Sustainable Chemistry & Engineering, 2013, vol. 1—pp. 419-426.
Stanzione et al, "Lignin Model Compounds as Bio-based Reactive Diluents for Liquid Molding Resins", ChemSusChem, 2012, vol. 5—pp. 1291-1297.
Stanzione et al., "Vanillin-based Resin for use in Composite Applications", Green Chemistry, 2012, vol. 14—pp. 2346-2352.
Sun, et al., "Bright Side of Lignin Depolymerization: Toward New Platform Chemicals", Chemical Reviews 2018, 118 (2)—pp. 614-678.
Tong et al., "Synthesis of Poly(methyl methacrylate)-b-poly(n-butyl acrylate-b-poly(methyl methacrylate) Triblocks and their Potential as Thermoplastic Elastomers", Polymer 2000, 41 (7)—pp. 2499-2510.
Van den Bosch et al., "Reductive Lignocellulose Fractionation into Soluble Lignin-Derived Phenolic Monomers and Dimers and Processable Carbohydrate Pulps", Energy & Environmental Science 2015, 8 (6)—pp. 1748-1763.
Vendamme et al., "Recent Synthetic Approaches and Emerging Bio-inspired Strategies for the Development of 34 Sustainable Pressure-sensitive Adhesives Derived from Renewable Building Blacks", Journal of Applied Polymer Science 2014, 131 (17), 40669—16 pages.
Wu et al., "Lignin Valorization: Two Hybrid Biochemical Routes for the Conversion of Polymerio Lignin into Value-added Chemicals", Scientific Reports 2017, 7 (1), 8420—13 pages.
Yamada et al., "Low Ceiling Temperature in Radical Polymerization of 2, 6-Dimethylphenyl Methacrylate", Journal of Macromolecular Science: Part A—Chemistry, vol. 15, Issue 2, 1981—1 page. (Abstract).
Calvaruso et al., "Biphasic extraction of mechanocatalytically-depolymerized lignin from water-soluble wood and its catalytic downstream processing", Green Chemistry 2017, 19 (12)—pp. 2893-2811.
Choi et al., "Fast pyrolysis of Kraft lignin-vapor cracking over various fixed-bed catalysts", Journal of Analytical and Applied Pyrolysis 2013, 100—pp. 207-212.
Deepa et al., "Lignin Depolymerization into Aromatic Monomers Over Solid Acid Catalysts", ACS Catalysis 2015, 5 (1)—pp. 365-379.
Deuss et al., "From Models to Lignin: Transition Metal Catalysis For Selective Bond Cleavage Reactians", J Coordination Chemistry Reviews, 2016, 306—pp. 510-532.
Ding et al., "High-Performance Pressure-Sensitive Adhesives From Renewable Triblock Copolymers", Biomacromolecules 2015, 16 (8) pp. 2537-2539.
Emerson et al., "Determination of Solvent-Polymer and Polymer-Polymer Flory-Huggins Interaction Parameters for Poly(3-hexylthlophene) Via Solvent Vapor Swelling", Macromolecules 2013, 46(16)—pp. 6533-6540.
Ferrini et al., "Catalytic Biorefining of Plant Biomass to Non-Pyrolytic Lignin Bio-oil and Carbohydrates Through Hydrogen Transfer Reactions", Angewandte Chemie, Int. Ed. 2014, vol. 53, pp. 8634-8639.
Gargallo et al., "Synthesis, Solution Properties and Chain Flexibility of Poly(2,6-Dimemylphenyl Methacrylate)" Polymer 1990, 31(5)—pp. 924-927.
Gotro et al, "Model Hydrocarbon Polymers: Rheological Properties of Linear Polyisoprenes and Hydrogenated Polyisoprenes", Macromolecules 1984, 17 (12)—pp. 2767-2775.

Holmberg et al., "Biobased Building blacks For The Rational Design of Renewable Block Polymers", Soft Matter 2014, 10 (38)—pp. 7405-7424.
Laurichesse et al., "Chemical Modification of Lignins: Towards Biobased Polymers", Progress in Polymer Science vol. 39, Issue 7, 2014—pp. 1268-1290.
Lee et al., "Preparation and Characterization of a Renewable Pressure-Sensitive Adhesive System Derived From: ε-48 Decalactone, L-lactide, Epoxidized Soybean Oil, and Rosin Ester", ACS Sustainable Chemistry & Engineering 2015, 3 (9)—pp. 2309-2320.
Liu et al., "Thermochemical Conversion of Lignin to Functional Materials: A Review and Future Directions", Green Chemistry 2015, 17 (11)—pp. 4888-4907.
Nakamura et al, "Tack and Viscoelastic Properties of an Acrylic Block Copolymer/Tackifier System", International Journal of Adhesion and Adhesives 2009, 29 (8)—pp. 806-811.
Nasiri et al., "Sustainable glucose-based block copolymers exhibit elastomeric and adhesive behavior", Polymer Chemistry 2016, 7 (33), pp. 5233-5240.
Rouméas et al., "Furylated flavonoids: fully biobased building blocks produced by condensed tannins depolymerization", ACS Sustainable Chemistry & Engineering 2018, 6 (1)—pp. 1112-1120.
Saito et al., "Turning Renewable Resources Into Value-Added Polymer: Development of Lignin-Based Thermoplastic", Green Chemistry 2012, 14 (12)—pp. 3295-3303.
Shin et al., "Pressure-Sensitive Adhesives From Renewable Triblock Copolymers", Macromolecules 2011, 44(1)—pp. 87-94.
Shuai et al., "Towards High-Yield Lignin Monomer Production", Green Chemistry 2017, 19 (16)—pp. 3752-3758.
Sinha, B., "Pressure Sensitive Adhesives Market By Chemical Composition (acrylic, rubber, ethylene vinyl acetate (EVA), silicone, polyurethane, and others), type (water based, hot melts, solvent based, and radiation based), application (labels, medical, graphics, tapes, and others) and end-use industry (automotive, packaging, building & construction, electronics, medical, consumer goods, and others)—global opportunity analysis and industry forecast, 2017-2023", https://www.alliedmarketresearch.com/pressure-sensitive-adhesives-market. (Accessed Mar. 5, 2018).
Song et al., "Hydrogenolysis of Lignosulfonate Into Phenols Over Heterogeneous Nickel Catalysts", Chemical Communications 2012, 48 (56)—pp. 7019-7021.
Tobing et al., "Molecular Parameters and Their Relation To The Adhesive Performance of Acrylic Pressure-Sensitive Adhesives", Journal of Applied Polymer Science 2001, 79 (12)—pp. 2230-2244.
Van de Pas et al., "Biobased Epoxy Resins From Deconstructed Native Softwood Lignin", Biomacromolecules 2017, 18 (8)—pp. 2640-2648.
Wang et al., "Effect of Methoxy Substituent Position on Thermal Properties and Solvent Resistance of Lignin-Inspired Poly(dimethoxyphenyl methacrylate)s", ACS Macro. Lett., 6 (8)—pp. 802-807.
Ye et al., "Selective Production of 4-Ethylphenolics from Lignin Via Mild Hydrogenolysis", Bioresource Technology 2012, 118—pp. 648-651.
Zhao et al., "Renewable Thermoplastics Based on Lignin-Derived Polyphenols", Macromolecules 2017, 50 (9)—pp. 3573-3581.
Roovers et al., "Characteristic Ratio and Plateau Modulus of 1,2-Polybutadiene. A Comparison With Other Rubbesr", Rubber Chemistry and Technology 1990, 63 (5)—pp. 734-746.
Pham et al., "Cinchona Based Squaramide Catalysed Enantioselective Michael Addition of α-Nitrophosphonates to Aryl Acrylates: Enantioselective Synthesis of Quaternary α-Aminophosphonates", Tetrahedron: Asymmetry, 2013, vol. 24, pp. 1605-1614.
Non Final Office Action for U.S. Appl. No. 16/277,473, dated Dec. 1, 2020, 14 pages.
Final Office Action for U.S. Appl. No. 16/277,473, dated Apr. 6, 2021, 12 pages.
Final Office Action for U.S. Appl. No. 16/277,473, dated Nov. 10, 2021, 9 pages.
Biswas, B., et al. "Total synthesis of alboatrin, a phytotoxic metabolite from Verticillium alboatrum", Tetrahedron 2008, 64, pp. 3212-3216.

(56) References Cited

OTHER PUBLICATIONS

Non Final Office Action for U.S. Appl. No. 16/277,473, dated Feb. 9, 2022, 14 pages.
Occelli, E. et al., "Synthesis of 4-alkenyl-3,5-dimethoxybenzoic acids by Claisen Rearrangement", Gazzetta Chimica Italiana, vol. 111 (9-10), 383-389 (Year: 1981).
Saá, J. et al., "Palladium-Catalyzed Cross-Coupling Reactions of Highly Hindered, Electron-Rich Phenol Tritiates and Organostannanes", J. Org. Chem., 57, 2, 678-685 (Year: 1992).
Final Office Action for U.S. Appl. No. 16/277,473, dated May 13, 2022, 9 pages.
Non Final Office Action for U.S. Appl. No. 16/277,473, dated Aug. 16, 2022, 7 pages.

* cited by examiner

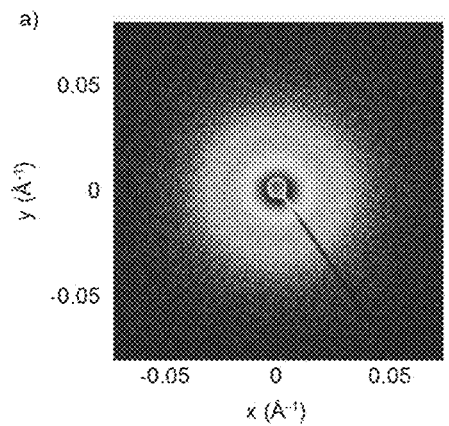 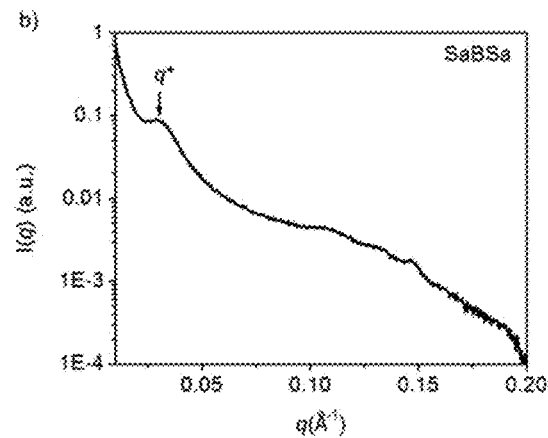
Fig. 6A　　　　　　　　Fig. 6B
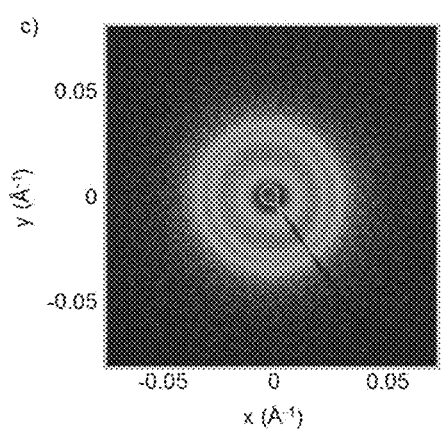 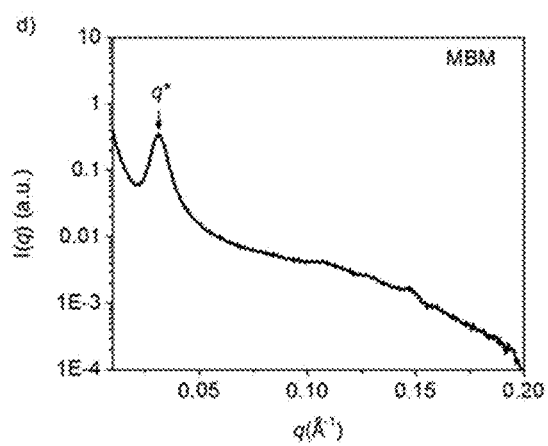
Fig. 6C　　　　　　　　Fig. 6D

BIO-BASED POLYMERS FROM RAW LIGNOCELLULOSIC BIOMASS

CROSS-REFERENCE TO RELATED APPLICATIONS

This application claims priority from United States Provisional Application Nos. 62/615,040, filed Jan. 9, 2018 and 62/713,571 filed Aug. 2, 2018; and is a continuation-in-part of U.S. patent application Ser. No. 15/208,135 filed Jul. 12, 2016, which claims priority from U.S. Provisional Application No. 62/191,551, filed Jul. 13, 2015. The disclosures of the aforementioned applications are incorporated herein by reference in their entirety for all purposes.

STATEMENT REGARDING FEDERALLY SPONSORED RESEARCH

This invention was made with government support under Grant Nos. DE-SC0014458 and DE-SC0001004 awarded by the Department of Energy and Grant No. CHE-1507010 awarded by the National Science Foundation. The government has certain rights in the invention.

FIELD OF THE INVENTION

The present invention relates to polymerizable bio-based monomers containing one phenolic hydroxyl group, which has been derivatized to provide at least one polymerizable functional group, which is an ethylenically unsaturated functional group, derived from raw lignin-containing biomass, bio-based copolymers prepared from such bio-based monomers and a co-monomer, and methods of making and using such bio-based copolymers. In particular, the present inventions relate to pressure sensitive adhesives, binders, and polymer electrolytes comprising the bio-based copolymers.

DESCRIPTION OF THE RELATED ART

To address sustainability challenges associated with petrochemicals, researchers have exploited a plethora of renewable chemicals to generate bio-based, cost-effective, and thermomechanically useful macromolecules. Lignin is one renewable resource that shows promise as a desirable alternative to petroleum feedstocks, largely due to its abundance as a byproduct of pulp and paper processing and biorefining. Corresponding lignin-based bio-oils (e.g., the volatile fraction of pyrolyzed lignin or the soluble fraction of depolymerized lignin) contain numerous aromatic compounds that structurally resemble common monomers (e.g., bisphenol A and styrene) for various polymer applications. The aromatic moieties in lignin are linked by several types of robust C=C and C—O bonds, and deconstruction of lignin therefore generates mixtures of disparate compounds (monophenols, dimers, and oligomers).[4,10-14] The exact structure and composition of a lignin-based bio-oil is highly variable, depending on the biomass resource, lignin type, and depolymerization route, among other factors. In general, the native components of all lignin-based bio-oils include phenols and guaiacols (2-methoxyphenols), whereas the native components of angiosperm (hardwood, e.g., oak and maple trees) and graminaceous (grassy, e.g., switchgrass and corn stover) bio-oils also include syringols (2,6-dimethoxyphenols).

Although bio-based model compounds, and in particular lignin model compounds have been extensively explored toward the formulation of new products for applications, such as thermoplastics, thermoplastic elastomers, coatings, pressure sensitive adhesives (PSAs), composites, and resins,[17-26] a major unanswered question remains—if these bio-based compounds can be harvested from raw biomass to produce designer materials in a scalable and cost-effective manner. Essentially, a significant gap exists between deriving well-defined chemicals from raw biomass and directly utilizing these chemicals for the formulation of specialized consumer products.

Hence, there is a need for a robust and scalable process for depolymerization, purification, functionalization, and polymerization, along with potential recycle and reuse of catalyst and solvents in the process, which are essential to reduce the energy and cost associated with 'green' materials fabrication and to encourage the sustained use of biomass-derived materials in mainstream applications.

BRIEF SUMMARY OF THE INVENTION

The present invention discloses a process for harnessing high purity aromatic compounds in high yield directly from the depolymerization of raw biomass for the preparation of advanced and high performance polymers for applications such as pressure sensitive adhesives (PSAs) and binders and electrolytes for lithium-ion batteries.

Various exemplary aspects of the present invention may be summarized as follows:

In an aspect, there is provided a method for producing a bio-based copolymer using bio-based monomers obtained from biomass material, wherein the method comprises:

a) contacting a biomass with a hydrogenolysis catalyst in the presence of hydrogen at a first temperature, thereby hydrogenolyzing the biomass to produce a mixture of depolymerized lignin products and residual feedstock components, wherein at least one of the mixture of depolymerized lignin products contains a phenolic hydroxyl group and has a structure corresponding to formula (I):

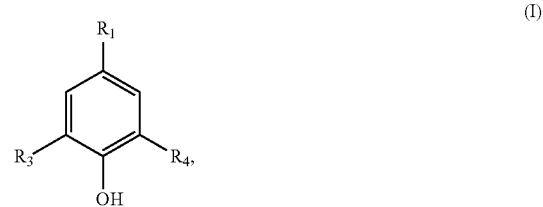

wherein $R_1$ is hydrogen, methyl, ethyl, n-propyl, i-propyl, propylene, formyl, a propanoate salt, a propanoate ester, an acetate salt, or an acetate ester (such as methyl acetate), and wherein $R_3$ and $R_4$ are independently selected from hydrogen or methoxy;

b) separating the mixture of depolymerized lignin products in a liquid stream from the residual feedstock components;

c) extracting at least one depolymerized lignin product containing a phenolic hydroxyl group from the liquid stream of the depolymerized lignin products, wherein optionally solvent is removed from the liquid stream before the extracting;

d) reacting the at least one extracted depolymerized lignin product containing a phenolic hydroxyl group with a functionalized reagent containing at least one functional group reactive with the phenolic hydroxyl group, thereby forming one or more bio-based monomers having a structure corresponding to formula (II):

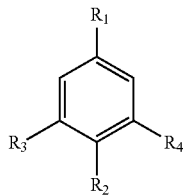

(II)

wherein $R_2$ is the substituent comprised of at least one polymerizable functional group which is an ethylenically unsaturated functional group; and e) forming a copolymer.

In an embodiment of the method, the hydrogenolysis catalyst comprises a catalyst comprising:

a. at least one of Ru, Ni, Pd, NiPd, NiRu, and RuPd supported on a support selected from the group consisting of carbon, alumina, silica, and alumina-silica, b. a metal sulfide selected from the group consisting of $CoS_2$, CoS, $MoS_2$, $WS_2$, and mixtures thereof, or c. a mixture thereof.

In another embodiment of the method, the functionalized reagent is selected from the group consisting of anhydrides, acyl halides, carboxylic acids, acrylamides, epoxies, and vinyls.

In yet another embodiment of the method, the functionalized reagent is [meth]acrylic anhydride, [meth]acrylic acid, or [meth]acryloyl chloride, and wherein the one or more polymerizable bio-based monomers comprises:

(i) a phenol [meth]acrylate selected from the group consisting of cresol [meth]acrylate, 4-ethylphenol [meth]acrylate, 4-propylphenol [meth]acrylate, 4-hydroxybenzaldehyde [meth]acrylate, and 3-(4-hydroxyphenol)propanoate [meth]acrylate;

(ii) a monomethoxyphenol [meth]acrylate selected from the group consisting of guaiacol (monomethoxy-substituted phenol) [meth]acrylate, 4-ethylguaiacol [meth]acrylate, creosol [meth]acrylate, 4-propylguaiacol [meth]acrylate, vanillin [meth]acrylate, and methyl homovanillate [meth]acrylate (methyl 2-(4-hydroxy-3-methoxyphenyl)acetate [meth]acrylate);

(iii) a dimethoxyphenol [meth]acrylate, or syringol (dimethoxy-substituted phenol) [meth]acrylate); or (iv) combinations thereof.

In an aspect of the method, the step of forming a bio-based copolymer comprises forming a block copolymer comprising at least one bio-based polymeric block comprising, in polymerized form, at least one bio-based monomer corresponding to formula (II) and a co-monomer-based polymeric block.

In an embodiment of the method, the co-monomer-based polymeric block comprises, in polymerized form, at least one of ethylene oxide, propylene oxide, (oligo-oxyethylene) [meth]acrylate, styrene trifluoromethanesulfonylimide lithium salt, 1-(3-(methacryloyloxy)-propylsulfonyl)-1-(trifluoromethylsulfonyl)imide lithium salt, and 3-sulfopropyl methacrylate lithium salt or comprises oligo-oxyethylene, oligo-oxypropylene, poly(ethylene oxide) or poly(propylene oxide).

In another embodiment of the method, the step of forming a block copolymer comprises forming a triblock copolymer having a midblock and two glassy end blocks, wherein the co-monomer-based polymeric block is the midblock and is formed by polymerizing a co-monomer comprising an alkyl [meth]acrylate, a diene, or an olefin and wherein at least one of the two glassy end blocks is formed by polymerizing the at least one bio-based monomer In yet another aspect of the method, the step of forming a bio-based copolymer comprises co-polymerizing at least one bio-based monomer corresponding to formula (II) with one or more co-monomers other than the at least one bio-based monomer.

In an embodiment, the one or more co-monomers comprises a co-polymerizable ion-conducting co-monomer, and wherein the copolymer is a random, statistical, graft, star, brush or cyclic copolymer.

In another embodiment, the co-polymerizable ion-conducting co-monomer comprises at least one of (oligo-oxyethylene) [meth]acrylate, styrene trifluoromethanesulfonylimide lithium salt, 1-(3-(methacryloyloxy)-propylsulfonyl)-1-(trifluoromethylsulfonyl)imide lithium salt, and 3-sulfopropyl methacrylate lithium salt.

In accordance with various embodiments of the method, the biomass is at least one of lignocellulose biomass, solid wood waste, forest wood waste, lignin rich food waste, energy crops, animal waste, agricultural waste, or lignin residue generated by cellulosic biorefinery or paper pulping industries.

In an aspect, there is provided a bio-based copolymer comprising in polymerized form:

(i) at least one polymerizable lignin-based monomer having a structure corresponding to formula (II):

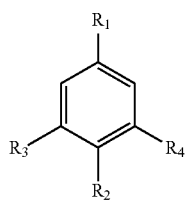

(II)

wherein $R_1$ is hydrogen, methyl, ethyl, n-propyl, i-propyl, propylene, formyl, propanoate salt, a propanoate ester, an acetate salt, or an acetate ester (e.g., methyl acetate), wherein $R_2$ is a substituent comprised of at least one polymerizable functional group which is an ethylenically unsaturated functional group, and wherein $R_3$ and $R_4$ are independently selected from hydrogen or methoxy; and (ii) at least one ion-conducting co-monomer other than the bio-based monomer.

In an embodiment of the bio-based copolymer, the bio-based copolymer is a block copolymer comprising at least one bio-based polymeric block comprising, in polymerized form, at least one bio-based monomer corresponding to formula (II) and an ion-conducting co-monomer-based polymeric block.

In another embodiment, the ion-conducting co-monomer-based polymeric block comprises, in polymerized form, at least one of ethylene oxide, propylene oxide, (oligo-oxyethylene) [meth]acrylate, styrene trifluoromethanesulfonylimide lithium salt, 1-(3-(methacryloyloxy)-propylsulfonyl)-1-(trifluoromethylsulfonyl)imide lithium salt, and 3-sulfopropyl methacrylate lithium salt or comprises at least one of oligo-oxyethylene, oligo-oxypropylene, poly(ethylene oxide), or poly(propylene oxide).

In one embodiment, the co-monomer-based polymeric block comprises a poly((oligo-oxyethylene) [meth]acrylate) block, and wherein the bio-based copolymer is a diblock bio-based copolymer having the following structure (III) or a triblock having the following structure (IV):

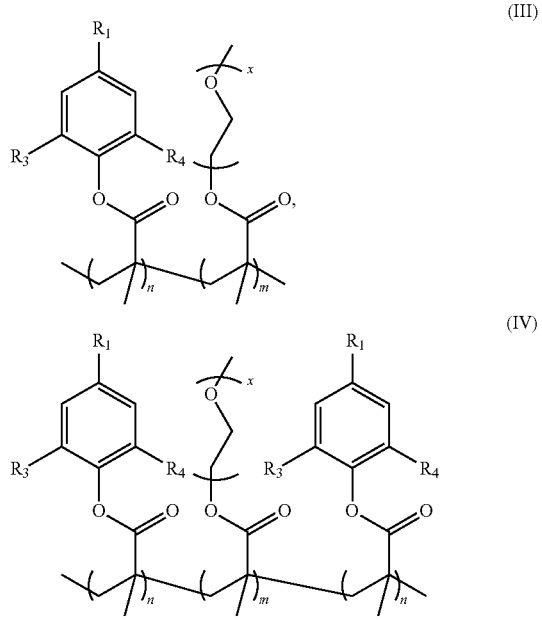

wherein x is in the range of 2-1000; n is in the range of 10-500; m is in the range of 10-1000; $R_1$ is hydrogen, methyl, ethyl, n-propyl, i-propyl, propylene, formyl, a propanoate salt, a propanoate ester, an acetate salt, or an acetate ester (e.g., methyl acetate); and $R_3$ and $R_4$ are independently selected from hydrogen or methoxy.

In an embodiment, the at least one ion-conducting co-monomer is a co-polymerizable co-monomer comprising at least one of (oligo-oxyethylene) [meth]acrylate, styrene trifluoromethanesulfonylimide lithium salt, 1-(3-(methacryloyloxy)-propylsulfonyl)-1-(trifluoromethylsulfonyl)imide lithium salt, and 3-sulfopropyl methacrylate lithium salt, and wherein the copolymer is a random, statistical, graft, star, brush, or cyclic copolymer.

In an aspect, there is provided a binder for a battery comprising the bio-based copolymer, as disclosed hereinabove.

In another aspect, there is provided an electrode comprising the binder, as disclosed hereinabove and an electrode active material.

In an embodiment of the electrode, the polymer electrolyte comprises the bio-based copolymer of the present invention and at least one salt.

In another embodiment, the at least one salt comprises at least one lithium salt selected from the group consisting of LiBr, LiCl, LiClO$_4$, LiPF$_6$, LiAsF$_6$, LiSbF$_6$, LiBF$_4$, LiCF$_3$SO$_3$, LiN(FSO$_2$)$_2$, LiN(CF$_3$SO$_2$)$_2$, LiN(C$_2$F$_5$SO$_2$)$_2$, LiC$_6$F$_3$N$_4$, LiC(CF$_3$SO$_2$)$_3$, Li$_2$B$_{10}$Cl$_{10}$, LiB(OCH$_3$)$_4$, LIB(C$_2$O$_4$)$_2$, LiB(CN)$_4$, LiBC$_2$O$_4$F$_2$, LiB(C$_3$O$_4$F)$_2$, lithium acetate, and LiAlCl$_4$.

In another aspect, there is provided an electrochemical device comprising an electrode in electrical contact with a polymer electrolyte, wherein at least one of the electrode and the polymer electrolyte comprises the bio-based copolymer of the present invention.

In an aspect, there is provided an article comprising an adhesive composition disposed over a substrate, wherein the adhesive composition comprises a bio-based block copolymer comprising:

(i) at least one bio-based polymeric block comprising, in polymerized form, at least one polymerizable bio-based monomer having a structure corresponding to formula (II):

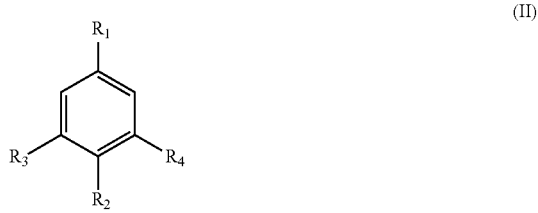

wherein $R_1$ is hydrogen, methyl, ethyl, n-propyl, i-propyl, propylene, formyl, a propanoate salt ester, a propanoate ester, an acetate salt, or an acetate ester (e.g., methyl acetate), wherein $R_2$ is a substituent comprised of at least one polymerizable functional group that is an ethylenically unsaturated functional group, wherein $R_3$ and $R_4$ are independently selected from hydrogen or methoxy, and wherein the ethylenically unsaturated functional group has been polymerized in the at least one bio-based polymeric block; and (ii) a co-monomer-based polymeric block comprising, in polymerized form, at least one co-monomer other than the at least one bio-based monomers, wherein the at least one co-monomer comprises an alkyl [meth]acrylate, a diene, or an olefin.

In an embodiment of the article, the at least one co-monomer comprises an alkyl [meth]acrylate containing an alkyl group selected from the group consisting of C1 to C18 alkyl groups.

In another embodiment, the block polymer is a bio-based triblock copolymer, having a midblock and two glassy end blocks, wherein the midblock is comprised of the alkyl [meth] acrylate in polymerized form and one or both of the glassy end blocks is or are comprised of the at least one bio-based monomer in polymerized form.

In yet another embodiment, $R_1$ is propyl and $R_3$ and $R_4$ are methoxy; and the triblock bio-based copolymer is poly(4-propylsyringyl acrylate-b-butyl acrylate-b-4-propylsyringyl acrylate) having the following structure (V):

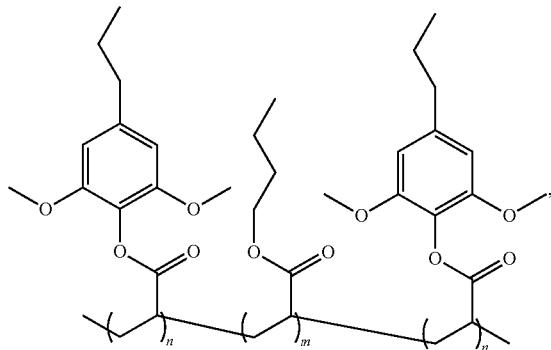

(V)

and
wherein n is in the range of 20-100; and m is in the range of 50-1000.

In one embodiment of the article, the adhesive composition is a pressure sensitive adhesive composition.

In another embodiment, the article further comprises one or more additives selected from the group consisting of tackifiers, plasticizers, viscosity modifiers, photoluminescent agent, anti-counterfeit and UV-reactive additives, dyes/pigments, anti-static materials, surfactants, and lubricants.

In another embodiment of the article, the substrate comprises a polymeric film, a paper label, a tape backing, a graphic article, a plastic article, a metal article, a wound dressing, a protection film or tape, or a release liner.

BRIEF DESCRIPTION OF THE DRAWINGS

FIGS. 6A-6D show a) 2D small angle X-ray scattering (SAXS) pattern and b) azimuthally-integrated 1D SAXS data for SaBSa [principal scattering peak, q*, at 0.030 Å$^{-1}$ (arrow), corresponding to a domain spacing (d*=2n/q*) of ~21 nm]; c) 2D SAXS pattern and d) azimuthally-integrated 1D SAXS data for MBM [q*=0.031 Å$^{-1}$ (arrow), corresponding to a domain spacing of ~20 nm].

DETAILED DESCRIPTION OF CERTAIN EMBODIMENTS OF THE INVENTION

Figure 1:
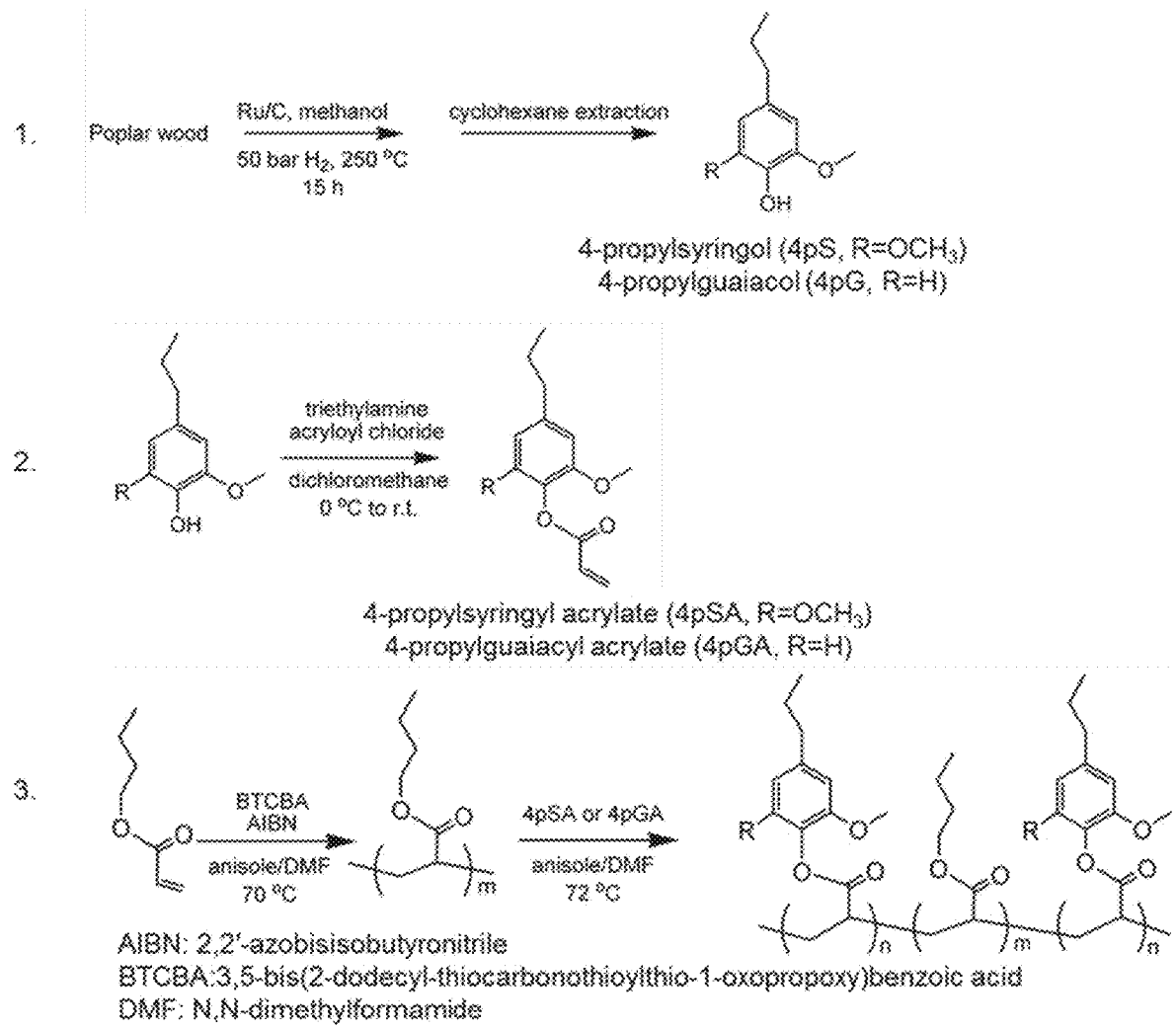
FIG. 1 shows a general process of forming a bio-based copolymer from raw biomass (4-propylsyringol: R=OCH$_3$; 4-propylguaiacol: R=H).

As used herein, the term "bio-based monomer" refers to a chemical compound containing one phenolic hydroxyl group that has been derivatized to provide at least one polymerizable functional group, which is an ethylenically unsaturated functional group, and which is derived from lignin-containing biomass, including, but not limited to, softwoods, lignocellulose biomass, solid wood waste, forest wood waste, lignin rich food waste, energy crops, animal waste, agricultural waste, or lignin residue generated by cellulosic biorefinery or paper pulping industries. Suitable lignin-rich food wastes include, but are not limited to nutshells, olive seeds, and tomato peels and seeds. Suitable energy crops include but are not limited to wheat, corn, soybean, sugarcane, *arundo*, camelina, carinate, jatropha, *miscanthus*, sorghum, and switchgrass.

Suitable polymerizable bio-based monomers of the present invention include, but are not limited to:

(i) an unsubstituted phenol [meth]acrylate or a substituted phenol [meth]acrylate, such as cresol [meth]acrylate, 4-ethylphenol [meth]acrylate, 4-propylphenol [meth]acrylate, 4-hydroxybenzaldehyde [meth]acrylate, or 3-(4-hydroxyphenol)propanoate [meth]acrylate, (ii) a monomethoxyphenol [meth]acrylate, such as guaiacol (monomethoxy-substituted phenol) [meth]acrylate, 4-ethylguaiacol [meth]acrylate, creosol [meth]acrylate, 4-propylguaiacol [meth]acrylate, vanillin [meth]acrylate, or methyl homovanillate [meth]acrylate (methyl 2-(4-hydroxy-3-methoxyphenyl)acetate [meth]acrylate), (iii) a dimethoxyphenol [meth]acrylate, such as a syringol [meth]acrylate, or (iv) combinations thereof.

As used herein, the terms "syringols" and "guaiacols" refer to phenolic compounds derived from depolymerized lignins containing one phenolic hydroxyl group and in addition two methoxy groups and one methoxy group respectively. Syringols, guaiacols, and phenols can be obtained from any suitable lignin-containing biomass, including, but not limited to, softwoods, lignocellulose biomass, solid wood waste, forest wood waste, lignin rich food waste, energy crops, animal waste, agricultural waste, or lignin residue generated by cellulosic biorefinery or paper pulping industries. Suitable examples of lignin-containing biomass include, for example and without limitation, oak, alder, chestnut, ash, aspen, balsa, beech, birch, boxwood, walnut, laurel, camphor, chestnut, cherry, dogwood, elm, eucalyptus, pear, hickory, ironwood, maple, olive, poplar, sassafras, rosewood, bamboo, coconut, locust, and willow trees, as well as, but not limited to, grasses (e.g., switchgrass, bamboo, straw), cereal crops (e.g., barley, millet, wheat), agricultural residues (e.g., corn stover, bagasse), and lignin-rich food wastes (e.g., nutshells, olive seeds, and tomato peels and seeds). Syringol, guaiacol, and phenol molecules can also come from petrochemical resources.

As used herein, the term "syringol" refers to a 2,6-dimethoxyphenol and the term "guaiacol" refers to a 2-methoxyphenol, with different moieties (including hydrogen) as substituents in the 4-position of the aromatic ring. A syringol and guaiacol thus corresponds to compounds having the following structures respectively:

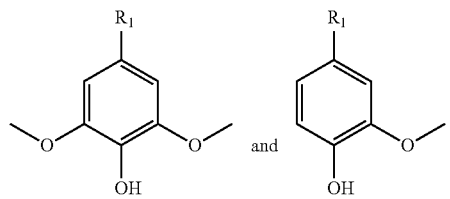

The p-position moiety ($R_1$) may be, for example, hydrogen (—H); alkyl groups (including linear, branched and cyclic alkyl groups, including C1-C3 alkyl groups (such as methyl, ethyl, n-propyl, and i-propyl), alkylene groups (such as propylene), formyl, propanoate (in salt or ester form), or acetate (in salt or ester form). Any of these moieties may be attached as substituents to the aromatic rings of other phenols within the scope of the present invention.

Method of Producing a Bio-Based Copolymer Using Lignin-Based Monomers

In an aspect of the invention, there is provided a method for producing a bio-based copolymer of the present invention, as disclosed hereinbelow, using bio-based monomers obtained from biomass material. The method may include a first step of contacting a biomass with a hydrogenolysis catalyst in the presence of hydrogen at a first temperature, thereby hydrogenolyzing the biomass to produce a mixture of depolymerized lignin products and residual feedstock components, wherein at least one depolymerized lignin product in the mixture of depolymerized lignin products contains one phenolic hydroxyl group and has a structure corresponding to formula (I):

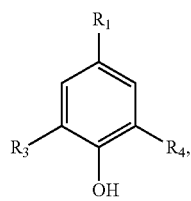

(I)

wherein $R_1$ is hydrogen, methyl, ethyl, n-propyl, i-propyl, propylene, formyl, a propanoate salt, a propanoate ester, an acetate salt, or an acetate ester (e.g., methyl acetate), and $R_3$ and $R_4$ are independently selected from hydrogen or methoxy.

In one embodiment, both $R_3$ and $R_4$ are hydrogen and the resulting depolymerized lignin product is a bio-derived phenol. In another embodiment, $R_3$ is hydrogen, and $R_4$ is methoxy group and the resulting depolymerized lignin product is a bio-derived the guaiacol. In another embodiment, both $R_3$ and $R_4$ are methoxy groups and the resulting depolymerized lignin product is a bio-derived syringol. In an embodiment, the mixture of depolymerized lignin products comprises a mixture of a bio-derived phenol, a bio-derived guaiacol and a bio-derived syringol.

Any suitable hydrogenolysis catalyst may be used, including, but not limited to a catalyst comprising:
  a. at least one of Ru, Ni, Pd, NiPd, NiRu, or RuPd supported on at least one support selected from the group consisting of carbon, alumina, silica, and alumina-silica,
  b. a metal sulfide selected from the group consisting of $CoS_2$, CoS, $MoS_2$, $WS_2$, or a mixture thereof, or
  c. a mixture thereof.

The method further comprises separating the mixture of depolymerized lignin products in a liquid stream from the residual feedstock components and extracting at least one depolymerized lignin product containing one phenolic hydroxyl group from the liquid stream of the depolymerized lignin products. In an embodiment, the depolymerized lignin products in a liquid stream may be separated by filtration from the residual feedstock components. Furthermore, the solvent in the liquid stream may be removed by any suitable method such as distillation, and the solid residue containing depolymerized lignin products may be contacted with at least one non-polar organic solvent, in particular a hydrocarbon solvent (e.g., an aliphatic hydrocarbon solvent such as cyclohexane or hexane) to extract the depolymerized lignin products containing one phenolic hydroxyl group.

The method further comprises reacting the at least one extracted depolymerized lignin product containing one phenolic hydroxyl group with a functionalized reagent containing at least one functional group reactive with the phenolic hydroxyl group, thereby forming one or more polymerizable bio-based monomers having a structure corresponding to formula (II):

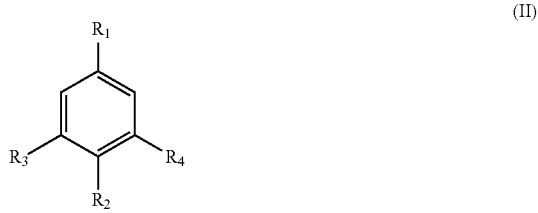

(II)

wherein $R_2$ is the substituent comprised of at least one polymerizable functional group, which is an ethylenically unsaturated functional group.

A "polymerizable bio-based monomer" in the context of the present invention is a bio-based monomer that has been modified to incorporate a moiety containing at least one polymerizable functionality (other than a hydroxyl group) at the phenol (—OH) position. The polymerizable functionality, in certain embodiments of the invention, is polymerizable through chain-growth polymerization mechanisms, such as free-radical and controlled-radical polymerization. In other embodiments, however, the polymerizable functionality is polymerizable through other mechanisms, such as anionic polymerization, cationic polymerization, condensation polymerization, ring-opening polymerization and so forth.

Polymerizable functionalities (e.g., for $R_2$) include, but are not limited to, ethylenically unsaturated functionalities such as methacrylate, acrylate, maleinate, maleate, fumarate, acrylamide, methacrylamide, vinyl, allyl, vinyl ester, and vinyl amide groups. These polymerizable groups can be attached to the bio-based precursors using acylation or esterification reactions between the phenol (aromatic hydroxyl group) and a reactive moiety (i.e., a moiety reactive with the phenol) bearing at least one polymerizable group (e.g., $R_2$). Reagents that can provide the new polymerizable group include, but are not limited to, anhydrides (e.g., methacrylic anhydride, acrylic anhydride, maleic anhydride), acyl halides (e.g., methacryloyl chloride, acryloyl chloride, fumaryl chloride).

The term [meth]acrylate or [meth]acrylamide, as used herein, means the monomer can be either an acrylate or methacrylate (in the case of a [meth]acrylate) or acrylamide or methacrylamide (in the case of a [meth]acrylamide). Preferred co-monomers, in certain embodiments of the invention, include those capable of providing bio-based copolymers which are glassy materials at room temperature (e.g., styrene and methyl [meth]acrylate) and/or other monomers that can be derived from lignin or other biomass materials (e.g., vanillin [meth]acrylate and other guaiacol [meth]acrylates). In one embodiment of the invention, a bio-based monomer (e.g., a phenol-based monomer, a guaiacol-based monomer, or a syringol-based monomer) is prepared by a method comprising reacting the depolymerized lignin product (e.g., a phenol, a guaiacol, or a syringol) containing one phenolic hydroxyl group with a functionalized reagent containing at least one polymerizable functional group other than a hydroxyl group (in particular, a polymerizable functional group which is an ethylenically unsaturated functional group, such as for example $-CH=CH_2$, $-C(=O)-CH=CH_2$, or $-C(=O)-C(CH_3)=CH_2$) and at least one functional group reactive with the phenolic hydroxyl group. For example, the functionalized reagent may be selected from the group consisting of anhydrides, acyl halides, carboxylic acids, acrylamides, epoxies, and vinyls. The polymerizable functional group may be selected from any of the above-mentioned polymerizable functionalities, particularly free radical-polymerizable functional groups, e.g., ethylenically unsaturated groups such as [meth] acrylates and vinyl groups. The functional group reactive with the phenolic hydroxyl group may be selected, for example, from the group consisting of anhydride groups, acyl halide groups, epoxy groups, carboxylic acid groups, ester groups, vinyl halide groups and the like. Methacrylic anhydride, acrylic anhydride, and maleic anhydride are examples of particularly preferred functionalized reagents. A catalyst may be present to promote the desired reaction between the phenolic hydroxyl group and the functional group reactive with the phenolic hydroxyl group. For example, when the functionalized reagent is an anhydride, a tertiary amine may be utilized as a catalyst, typically at a concentration of from about 0.01 to about 0.1 mol/mol tertiary amine/anhydride. It may be advantageous to react the anhydride and the depolymerized lignin product containing one phenolic hydroxyl group (e.g., a phenol, a guaiacol, or a syringol) at an approximately 1:1 molar ratio or with the anhydride in a slight molar excess relative to the depolymerized lignin product containing one phenolic hydroxyl group. For example, the molar ratio of anhydride: depolymerized lignin product containing one phenolic hydroxyl group can be from about 1:1 to about 1.2:1. An inhibitor may be present during reaction of the depolymerized lignin product and the functionalized reagent, to stabilize the bio-based monomer thereby formed and to reduce the extent of degradation or byproduct formation. Suitable inhibitors include, but are not limited to, sterically hindered alkylated phenols such as t-butyl-substituted phenols; typically, it will be desirable for about 500 ppm to about 3000 ppm of inhibitor to be present, based on the weight of the functionalized reagent. The reaction of the depolymerized lignin product containing one phenolic hydroxyl group and functionalized reagent may be carried out in bulk or in an inert organic solvent such as toluene or tetrahydrofuran. The reaction temperature may be from about room temperature (about 25° C.) to about 100° C., for example. The reaction between the depolymerized lignin product and the functionalized reagent is allowed to proceed at the desired temperature for a time effective to achieve the desired degree of conversion of the starting materials to the bio-based monomer (typically, about 1 hour to about 100 hours). The reaction product, containing the bio-based monomer, thereby obtained may then be worked up and purified using any of the techniques known in the field of organic chemistry, including washing a solution of the reaction product in a water immiscible organic solvent with one or more volumes of water (which may be neutral, acidic and/or basic), neutralization, concentration (removal of solvent, by distillation for example), fractionation, precipitation, (re)crystallization, distillation, and/or chromatography and the like. It will generally be advantageous to purify the bio-based monomer to a molar purity of at least 99% prior to utilizing the bio-based monomer in a polymerization, although lower purities can be used if the impurity(ies) do(es) not negatively impact the desired polymerization.

In one embodiment, the functionalized reagent is [meth] acrylic anhydride, [meth]acrylic acid or [meth]acryloyl chloride, and the one or more polymerizable bio-based monomers comprises:
  (i) a phenol [meth]acrylate selected from the group consisting of cresol [meth]acrylate, 4-ethylphenol [meth] acrylate, 4-propylphenol [meth]acrylate, 4-hydroxybenzaldehyde [meth]acrylate, and 3-(4-hydroxyphenol)propanoate [meth]acrylate;
  (ii) a monomethoxyphenol [meth]acrylate selected from the group consisting of guaiacol (monomethoxy-substituted phenol) [meth]acrylate, 4-ethylguaiacol [meth] acrylate, creosol [meth]acrylate, 4-propylguaiacol [meth]acrylate, vanillin [meth]acrylate, and methyl homovanillate [meth]acrylate (Methyl 2-(4-hydroxy-3-methoxyphenyl)acetate [meth]acrylate);
  (iii) a dimethoxyphenol [meth]acrylate, or syringol (dimethoxy-substituted phenol) [meth]acrylate); or
  (iv) combinations thereof.

In accordance with various embodiments of the present invention, the method also comprises forming a bio-based copolymer. As used herein, the term "bio-based copolymer" refers to an oligomeric or macromolecular molecule comprised of at least one bio-based monomer unit that has been polymerized at least by reaction of the polymerizable functional group(s) present in the monomer.

In an embodiment, the step of forming a bio-based copolymer comprises forming a bio-based block copolymer comprising at least one bio-based polymeric block comprising, in polymerized form, at least one bio-based monomer corresponding to formula (II) and a co-monomer-based polymeric block.

In another embodiment, the step of forming a bio-based copolymer comprising co-polymerizing at least one bio-based monomer corresponding to formula (II) with one or more co-monomers other than the at least one bio-based monomer In accordance with the present invention, the forming of a bio-based copolymer may further comprise the use of one or more difunctional or multifunctional co-monomers to make graft, brush-like, and star-like materials. Bio-based monomers with modified $R_1$ groups may provide an even greater range of properties than those accessible through bio-based monomers with native $R_1$ groups.

Bio-based copolymers in accordance with the present invention are not particularly limited with respect to their molecular weights or their geometry. For example, the bio-based copolymer may be either relatively low in molecular weight (oligomeric) or relatively high in molecular weight. The number average molecular weight of the bio-based copolymer may range from about 1000 daltons to about 5,000,000 daltons or even higher, for instance. The dispersity of the bio-based copolymer may be relatively low (e.g., less than 1.5, for example) or relatively high (e.g., 1.5 or greater). The bio-based copolymer may be, for example, linear, branched or even cross-linked in structure, depending upon the polymerization conditions, initiators, and monomers used. The bio-based copolymer may be a bio-based block copolymer, a random (statistical) bio-based copolymer, a graft bio-based copolymer, a brush bio-based copolymer, a star bio-based copolymer, or the like.

Bio-based copolymers in accordance with the present invention may be synthesized by any number of polymerization techniques including, but not limited to, free-radical polymerization, controlled-radical polymerization, atom-transfer radical polymerization (ATRP) and variants, single-electron transfer living radical polymerization (SET-LRP), reversible addition-fragmentation chain-transfer (RAFT) polymerization, ring-opening [metathesis] polymerization (RO[M]P), step-growth polymerization, cationic polymerization, anionic polymerization, coordination polymerization, condensation polymerization, emulsion polymerization, suspension polymerization, Ziegler-Natta polymerization, metallocene polymerization, group-transfer polymerization, reversible-deactivation radical polymerization, stable free radical polymerization (SFRP), TEMPO polymerization, cobalt-mediated radical polymerization, nitroxide-mediated radical polymerization (NMP), catalytic chain-transfer polymerization, iniferter polymerization, iodine-transfer polymerization (ITP), selenium-centered radical-mediated polymerization, telluride-mediated polymerization, stibine-mediated polymerization, cationic ring-opening polymerization, and/or catalyst-transfer polycondensation.

In a particular preferred embodiment, RAFT polymerization is employed to prepare a bio-based copolymer in accordance with the present invention. A bio-based copolymer may be prepared by a method comprising polymerizing at least one bio-based monomer via RAFT, in the presence of a free radical initiator and a chain transfer agent, to form the bio-based copolymer. One or more co-monomers may optionally also be polymerized, either together as a mixture with the bio-based monomer(s) or separately (sequentially or step-wise). RAFT polymerization is one of several kinds of reversible-deactivation radical polymerizations. It makes use of a chain transfer agent, such as a thiocarbonylthio compound (e.g., a dithioester, a thiocarbamate or a xanthate, such as 2-cyano-2-propyl benzodithioate), to afford control over the generated molecular weight and polydispersity during a free-radical polymerization. The chain transfer agent mediates the polymerization of the bio-based monomer(s) and optional co-monomers via a reversible chain-transfer process. The free-radical initiator may be, for example, an azo compound such as 2,2'-azobisisobutyronitrile (AIBN) or 4,4'-azobis(4-cyanovaleric acid) (ACVA). The polymerization may be carried out in an organic solvent or mixture of organic solvents, such as anisole, typically at temperatures ranging from about 40° C. to about 120° C., or alternatively with no solvent (bulk). The polymerization also can be carried out as an emulsion-type polymerization wherein one or more emulsification agents and a solvent (e.g., water) are used. Typical for RAFT polymerizations, 0.02 to 0.4 moles of initiator may be used for each mole of chain transfer agent; the moles of chain transfer agent relative to the number of monomer(s) depends upon the target molecular weight and the monomer-to-polymer conversion. As with other controlled radical polymerization techniques, RAFT polymerizations can be performed with conditions to favor low dispersity (narrow molecular weight distribution) and a pre-chosen molecular weight. RAFT polymerization can be used to design polymers of complex architectures, such as linear block copolymers, comb-like, star, brush polymers, dendrimers and cross-linked networks.

Suitable co-monomers for forming the bio-based copolymers include, but are not limited to:

a). other lignin-based monomers (2,6-dimethoxyphenol, 2-methoxyphenol, and phenol derivatives with varying 4-position moieties) with similar structures and functionalities as the phenol-based monomers;

b). styrenes (styrene, 4-bromostyrene, 4-fluorostyrene, etc.); alkylstyrenes (4-methylstyrene, 2-methylstyrene, 2,4-dimethylstyrene, 4-ethylstyrene, benzhydrylstyrene, etc.);

c). phenyl [meth]acrylates with any number and position of substituents and especially those also derived or obtained from lignin (e.g., phenyl [meth]acrylate, 2-methylphenyl [meth]acrylate, 4-ethylphenyl [meth]acrylate, 4-methylphenyl [meth]acrylate, 4-propylphenyl [meth]acrylate, guaiacol [meth]acrylate, creosol [meth]acrylate, 4-ethylphenyl [meth]acrylate, 4-propylguaiacyl [meth]acrylate, eugenol [meth]acrylate, vanillin [meth]acrylate, trimethoxysilylpropyl [meth]acrylate, and the like);

d). alkyl [meth]acrylates with alkyl chain lengths anywhere from 1 to 36 carbon atoms and any number of unsaturated bonds and especially those that are derived or obtained from bio-based resources (e.g., methyl [meth]acrylate, ethyl [methyl]acrylate, propyl [meth]acrylate, butyl [meth]acrylate, lauryl [meth]acrylate, palmitic [meth]acrylate, stearic [meth]acrylate, oleic [meth]acrylate, linoleic [meth]acrylate, and the like);

e). other types of [meth]acrylates (e.g., [meth]acrylic acid, perfluorooctyl [meth]acrylates, hydroxymethyl [meth]acrylate, hydroxyethyl [meth]acrylates, poly(oligo-ethylene glycol) [meth]acrylate, 3-sulfopropyl [meth]acrylate potassium salt, and the like);

f). terephthalates (e.g., polyethylene terephthalate, dimethyl terephthalate, butylene terephthalate, trimethylene terephthalate, dioctyl terephthalate, cyclohexylenedimethylene terephthalate, terephthalic acid, terephthaloyl chloride, and the like);

g). amides, amines, diamides, and diamines (e.g., hexamethylenediamine, diaminohexane, ethylenediamine, para-phenylenediamine, 4,4'-oxydianiline, putrescine, tetramethylene diamine, 2-methylpentamethylene diamine, trimethyl hexamethylene diamine, xylylene diamine, 1,5-pentadiamine, 11-aminoundecanoic acid, aminolauric acid, bis[para-aminocyclohexyl] methane, diethyltoluenediamine, dimethylthiotoluenediamine, triethanolamine, and the like);

h). dichlorides (e.g., hexanedioyl dichloride);

i). nitriles (e.g., acrylonitrile, 2-propenenitrile, methacrylonitrile, 2,6-dichlorobenzonitrile, pentachlorobenzonitrile);

j). carboxylic acids, including monocarboxylic acids, dicarboxylic acids and polycarboxylic acids (e.g., adipic acid, sebacic acid, terephthalic acid, isophthalic acid, dodecanedoic acid, 4-hydroxybenzoic acid, 6-hydroxynaphthalene-2-carboxylic acid, and the like);

k). lactones and lactone analogues (e.g., acetolactone, propiolactone, butyrolactone, valerolactone, caprolactone, dodecalactone, butenolide, macrolide, cardenolide, bufadienolide, lactide, cyclopentadenolide, coumarin, carvomenthide, menthide, tulipalin A, and the like), l). lactams (e.g., caprolactam, laurolactam, vinylcaprolactam, and the like);

m). maleates, malonates, and maleinates (e.g., dioctyl maleate, maleic acid, dimethyl maleate, maleic anhydride, diallyl maleate, diethyl allylmalonate) and associated isomers, such as fumarates;

n). vinyls (e.g., vinyl chloride, vinyl bromide, vinyl fluoride, 4-vinyl-styrene, ethylene, vinyl acetylene, vinyl naphthalene, vinylpyridine, vinylformamide, and the like);

o). vinyl esters (e.g., vinyl acetate, vinyl benzoate, vinyl 4-tert-butylbenzoate, vinyl chloroformate, vinyl cinnamate, vinyl decanoate, vinyl nenodecanoate, vinyl nenononanoate, vinyl pivalate, vinyl propionate, vinyl stearate, vinyl trifluoroacetate, vinyl valerate, and the like);

p). vinyl amides (e.g., N-methyl-N-vinylacetamide, vinylformamide, vinylacetoamide, vinyl amide, and the like);

q). [meth]acrylamides (e.g., alkyl [meth]acrylamides, butyl [meth]acrylamide, diacetone [meth]acrylamide, diethyl [meth]acrylamide, diethyl [meth]acrylamide, ethyl [meth]acrylamide, hexamethylenebis[meth]acrylamide, hydroxymethy[meth]acrylamide, hydroxyethyl [meth]acrylamide, isobutoxymethyl [meth]acrylamide, isopropyl [meth]acrylamide, [meth]acrylamide, phenyl [meth]acrylamide, triphenylmethyl [meth]acrylamide, and the like);

r). thiols, dithiols, and polythiols (e.g., butanedithiol, benzenedithiol, biphenyldithiol, benzenetrithiol, decanedithiol, dithiothreitol, dithioerythritol, dimercaptonaphthalene, ethanedithiol, hexanedithiol, octanedithiol, propanedithiol, pentanedithiol, thiobisbenzenethiol, and the like);

s). enes, dienes, and olefins (e.g., terpenes, sesquiterpenes, ethylene, propene, butylene, isoprene, acetylene, myrcene, humulene, caryophyllene, farnesene, limonene, methylpentene, ethylene, propylene, butadiene, decalene, tetrafluoroethylene, hexafluoropropylene, pinene, chloroprene, acetylene, and the like);

t). allyl monomers (e.g., allyl acetate, allyl acetoacetate, allyl alcohol, allylamine hydrochloride, allyl benzyl ether, allyl 2-bromo-2-methylpropionate, allyl butyl ether, allyl chloroacetate, allyl cyanide, allyl cyanoacetate, allyl ether, allyl ethyl ether, allyl methyl carbonate, allyl methyl sulfone, allyloxybenzaldehyde, allyloxyethanol, allyoxy propanediol, allyl phenyl ether, allylphosphonic acid monoammonium salt, allyl trifuloroacetate, tert-butyl allyl carbamate, butyne, diallyl carbonate, methylsulfonyl propyne, propyne, trimethylolpropane [di]allyl ether, and the like, including the [meth]allyl analogues thereof);

u). azides and diazides (ethynylene diazide, glycidyl azide, etc.);

v). phosgene;

w). carbonates, including cyclic carbonates;

x). carbamates;

y). succinates;

z). alcohols, including diols and polyols (e.g., 4-amino-4-3-hydroxypropyl-1,7-heptanediol, benzenedimethanol, biphenyldimethanol, bis-hydroxymethyl-butyric acid, dihydrobenzoic acid, propanediol, cyclohexanediol, cyclopentanediol, dihydroxybenzophenone, dihydroxyacetophenone, dihydroxynaphthalene, butanediol, catechol, hexanediol, hexanetriol, hydrobenzoin, hydroquinone bis-2-hydroxyethyl ether, 2-hydroxymethyl-1,3-propanediol, pentanediol, phenyl-1,2-propanediol, ethylene glycol, pentaerythritol, glycerol, trimethylolpropane, and the like);

aa). silanes, silicones, and siloxanes (e.g., dimethyldichlorosilane, silatrane glycol, tetramethyl-tetravinylcyclotetrasiloxane, and the like);

bb). ethers and vinyl ethers (e.g., vinyl ether, [di]glycidyl ether, butanediol [di]vinyl ether, butyl vinyl ether, chlorethyl vinyl ether, cyclohexyl vinyl ether, dodecyl vinyl ether, diethyl vinyl orthoformate, diethylene glycol [di]vinyl ether, phenyl vinyl ether, propyl vinyl ether, isobutyl vinyl ether, ethyl vinyl ether, ethylhexyl vinyl ether, ethylene glycol vinyl ether, and the like);

cc). vinyl sulfides (e.g., vinyl sulfide, phenyl vinyl sulfide, 4-chlorophenyl vinyl sulfide, bromphenyl vinyl sulfide, ethyl vinyl sulfide, and the like);

dd). isocyanates, including diisocyanates and polyisocyanates (e.g., diisocyanatobutane, diisocyanatododecane, diisocyanatooctane, hexamethylene diisocyanate, cyclohexylene diisocyanate, phenylene diisocyanate, tolylene diisocyanate, toluene diisocyanate, methylene diphenyl diisocyanate, isophorone diisocyanate, and the like);

ee). epoxides (e.g., ethylene oxide, allyl glycidyl ether, butadiene diepoxide, butanediol diglycidyl ether, butyl glycidyl ether, tert-butyl glycidyl ether, chlorophenyl glycidyl ether, cyclohexene oxide, cyclopentene oxide, dicyclopetadiene dioxide, dieldrin, diepoxycyclooctane, diepoxyoctane, N,N-diglycidyl-4-glycidyloxyaniline, epoxybutane, epoxybutene, epoxydodecane, epoxyhexane, epoxyhexene, epoxynorbornane, epoxyoctane, epoxypentane, epoxy-phenoxypropane, epoxypropyl benzene, epoxypropyl phthalimide, epoxytetradecane, ethylhexyl glycidyl ether, furfuryl glycidyl ether, glycidyl 4-methoxyphenyl ether, glycidyl methylphenyl ether, methyl vinyloxirane, pinene oxide, propylene oxide, resorcinol diglycidyl ether, stilbene oxide, styrene oxide, and the like);

ff). norbornenes (e.g., dicyclopentadiene, norbornene, bicycloheptadiene, and the like); and gg). anhydrides (e.g., [meth]acrylic anhydride, maleic anhydride, citraconic anhydride, crotonic anhydride, itaconic anhydride, methylglutaric anhydride, methylphthalic anhydride, methylsuccinic anhydride, naphthalic anhydride, phenylglutaric anhydride, phenylmaleic anhydride, and the like);

as well as combinations or mixtures of any two or more of the above-mentioned co-monomers.

In an embodiment of the method, the step of forming a bio-based copolymer comprises forming a bio-based block copolymer, and wherein the co-monomer-based polymeric block comprises, in polymerized form, at least one of ethylene oxide, propylene oxide, (oligo-oxyethylene) [meth] acrylate, styrene trifluoromethanesulfonylimide lithium salt, 1-(3-(methacryloyloxy)-propylsulfonyl)-1-(trifluoromethylsulfonyl)imide lithium salt, and 3-sulfopropyl methacrylate lithium salt or comprises at least one of oligo-oxyethylene, oligo-oxypropylene, poly(ethylene oxide) or poly(propylene oxide).

In another embodiment, the step of forming a bio-based block copolymer comprises forming a triblock copolymer, and wherein the co-monomer-based polymeric block is a midblock formed by polymerizing a co-monomer comprising an alkyl [meth]acrylate, a diene, or an olefin and wherein the at least one bio-based monomer is polymerized forming at least one of the two glassy end blocks.

In another embodiment, the step of forming a bio-based copolymer comprising co-polymerizing at least one bio-based monomer corresponding to formula (II) with one or more co-monomers other than the at least one bio-based monomer. In one embodiment, the one or more co-monomers comprises a co-polymerizable ion-conducting co-monomer, and wherein the copolymer is a random, statistical, graft, star, brush or cyclic copolymer. Suitable co-polymerizable ion-conducting co-monomer includes, but are not limited to, at least one of (oligo-oxyethylene) [meth] acrylate, styrene trifluoromethanesulfonylimide lithium salt, 1-(3-(methacryloyloxy)-propylsulfonyl)-1-(trifluoromethylsulfonyl)imide lithium salt, and 3-sulfopropyl methacrylate lithium salt.

The bio-based copolymer may, in a preferred embodiment, be a thermoplastic, but may in another embodiment be a thermoset. The bio-based monomers of the present invention also are useful in the preparation of thermoplastic elastomers, in particular thermoplastic elastomers which are bio-based block copolymers in which one or more blocks are blocks of one or more bio-based monomers providing a "hard" polymerized segment having a relatively high $T_g$ (e.g., a $T_g$ of at least 50° C. or more preferably a $T_g$ of at least 100° C.) and one or more blocks are blocks of a monomer or mixture of monomers providing a "soft" polymerized segment having a relatively low $T_g$ (e.g., a $T_g$ of less than 30° C. or more preferably a $T_g$ of less than 0° C.). As used herein the term "glassy end block" refers to those end blocks, which when formed into an independent polymer would result in a glassy polymer at the use temperature.

The bio-based copolymer may be comprised, in various embodiments of the invention, of at least 1%, at least 5%, at least 10%, at least 20%, at least 30%, at least 40%, at least 50%, at least 60%, at least 70%, at least 80%, at least 90%, at least 95%, or at least 99% by weight or 100% by weight of bio-based monomer(s) in polymerized form. The balance of the bio-based copolymer may be comprised of one or more of the above-mentioned co-monomers, in polymerized form, as well as initiator moieties and/or crosslinker moieties (to be extent initiators and/or crosslinking agents are used in the preparation of the bio-based copolymer and end up being incorporated into the bio-based copolymer as a result of the polymerization).

The bio-based copolymer may also be grafted to or grafted from particles, nanoparticles, and/or surfaces including, but not limited to, linoleum, granite, gold, concrete, silica, silicon dioxide, poly(dimethylsiloxane), poly(norbornene)s, poly(carbonate)s, graphene, graphite, diamond, garnet, ruby, emerald, topaz, talc, glass, zinc, steel, asphalt, ceramics, porcelain, tin, aluminum, foil, cloth, cotton, cellulosic fibers, lignin fibers, tetrafluoroethylene polymers, polyimides, quartz, nylon, silk, rayon, carbon nanotubes, nanowires, clay, and other organic, inorganic, or metalloorganic surfaces of varying roughness, flexibility, strength, and size. As used herein, the term "metallo-organic" refers to materials containing metal-organic bonds including, but not limited to metal organic frameworks and metal organic polyhedral.

The bio-based copolymer may also be a bulk or composite material. Many different nanoparticles and nanofibers may be blended into a bio-based copolymer before, during or after polymerization to impart different or enhanced properties to the product material. Nanoparticles and nanofibers of any of the above-mentioned types of materials or substances may be utilized as media from which, or to which, a bio-based copolymer may be synthesized or attached/grafted.

The bio-based copolymers, as disclosed hereinabove, may be used for various applications, especially as binders and electrolytes for lithium ion batteries and in articles as adhesives or as components of formulated adhesives.

A Bio-Based Copolymer for Use as a Binder or an Electrolyte

In an aspect, there is provided a bio-based copolymer comprising at least one polymerizable bio-based monomer having a structure corresponding to formula (II) as disclosed hereinabove and at least one ion-conducting co-monomer other than the polymerizable bio-based monomer. The bio-based copolymer can be a random, a statistical, or a bio-based block copolymer. However, in other embodiments, the bio-based copolymer can be a graft, a star, a brush, or a cyclic bio-based copolymer.

In one embodiment, the bio-based copolymer is a bio-based block copolymer. In particular, bio-based block copolymers of the present invention for use as polymer electrolytes and or binders provide several advantages, including but not limited to, being derived from renewable resources (bio-derived), adhesivity, thermal stability, and being operable at higher temperature than conventional materials such as polystyrene, thereby increasing stability and providing an opportunity to increase conductivity by increasing operating temperature. Furthermore, the bio-based block copolymers of the present invention can be capable of self-assembly into periodically ordered structures, which in turn provides simultaneous control over both ionic transport and mechanical strength (and thermal stability).

In an embodiment, the bio-based copolymer is a block copolymer comprising at least one bio-based polymeric block comprising, in polymerized form, at least one bio-based monomer corresponding to formula (II) and an ion-conducting co-monomer-based polymeric block. In such embodiments, the ion-conducting co-monomer-based polymeric block comprises, in polymerized form, at least one of ethylene oxide, propylene oxide, (oligo-oxyethylene) [meth] acrylate, styrene trifluoromethanesulfonylimide lithium salt, 1-(3-(methacryloyloxy)-propylsulfonyl)-1-(trifluoromethylsulfonyl)imide lithium salt, and 3-sulfopropyl methacrylate lithium salt or comprises at least one of oligo-oxyethylene, oligo-oxypropylene, poly(ethylene oxide), or poly(propylene oxide).

In another embodiment, the at least one ion-conducting co-monomer is a co-polymerizable ion-conducting co-monomer comprising at least one of (oligo-oxyethylene) [meth]acrylate, styrene trifluoromethanesulfonylimide lithium salt, 1-(3-(methacryloyloxy)-propylsulfonyl)-1-(trifluoromethylsulfonyl)imide lithium salt, and 3-sulfopropyl methacrylate lithium salt, and wherein the resulting bio-based copolymer is a random, statistical, graft, star, brush or cyclic copolymer. According to certain embodiments, the co-polymerizable ion-conducting co-monomer may have the following structure:

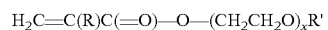

wherein R is H or $CH_3$, R' is H or alkyl (e.g., $C_1$-$C_6$ alkyl, such as methyl), and x is at least 2 (e.g., 2 to 1000). In certain embodiments, x is in the range of 2-1000, or 4-20, or 6-12.

Any suitable overall molar ratio of bio-based monomer to ion-conducting co-monomer in the bio-based copolymer may be used, including but not limited to, for example, within a range from 1:30 to 30:1, a range from 1:20 to 20:1, or a range from 1:10 to 10:1.

The number average molecular weights of the individual blocks or segments in the bio-based copolymer may be, for example, within a range of 1,000 to 500,000 g/mol. In one embodiment, the number average molecular weight of the bio-based monomer block is 5,000 to 25,000 g/mol, and the number average molecular weight of the ion-conducting co-monomer block is 1,000 to 15,000 g/mol.

In one embodiment, the bio-based monomer block portion(s) of the bio-based copolymer may be characterized as being essentially free or entirely free of any polymerized units of ion-conducting co-monomer. In one aspect, the bio-based monomer block portion(s) contain only polymerized units of one or more types of bio-based monomer. However, in other embodiments of the invention, it is possible for the bio-based monomer blocks to contain relatively small amounts (e.g., up to about 20 weight %) of polymerized units of monomers other than bio-based monomers such as, for example, [meth]acrylates, vinyl monomers, vinyl aromatic monomers, [meth]acrylamides, dienes, acrylonitrile, olefins and the like.

In one embodiment, the ion-conducting co-monomer block portion(s) of the bio-based copolymer may be characterized as being essentially free or entirely free of any polymerized units of bio-based monomer. In one aspect, the ion-conducting co-monomer block portion(s) contain only polymerized units of one or more types of ion-conducting co-monomer. However, in other embodiments of the invention, it is possible for the ion-conducting co-monomer blocks to contain relatively small amounts (e.g., up to about 20 weight %) of polymerized units of monomers other than ion-conducting co-monomers such as, for example, hydroxyalkyl esters of (meth)acrylic acid, (meth)acrylic acid, mono(oxyalkylene) acrylates and the like.

Generally speaking, it will be desirable for the bio-based copolymer to have a relatively low dispersity (sometimes also referred to as polydispersity index and calculated by dividing the weight average molecular weight by the number average molecular weight). For example, the dispersity of the bio-based copolymer in various embodiments of the present invention may be less than 1.5, less than 1.4, less than 1.3 or less than 1.2. Number average molecular weight and weight average molecular weight may be measured using gel permeation chromatography (GPC) and calibration standards such as polystyrene.

In one desirable embodiment of the invention, the composition of the bio-based copolymer (e.g., bio-based monomer and ion-conducting co-monomer used to prepare the bio-based copolymer, the molecular weight characteristics of the overall bio-based copolymer and the individual blocks or segments) is selected so as to provide a bio-based copolymer that is solid at room temperature and thermoplastic.

In one embodiment, the co-monomer-based polymeric block comprises a poly((oligo-oxyethylene) [meth]acrylate) block, and the bio-based copolymer is a diblock bio-based copolymer having the following structure (III) or a triblock bio-based copolymer having the following structure (IV):

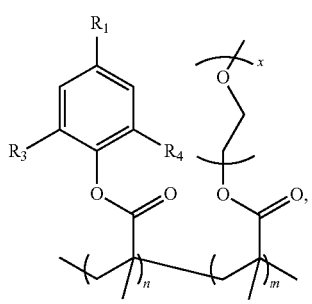

(III)

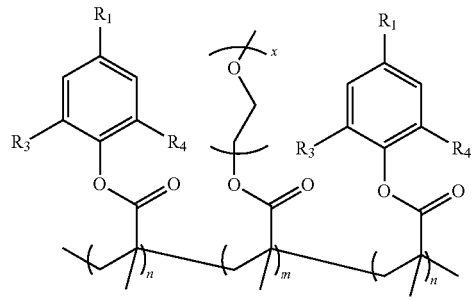

(IV)

wherein x is in the range of 2-1000, or 4-20, or 6-12; n in the range of 10-500, or 15-100, or 20-50; and m in the range of 10-1000, or 15-200, or 20-50.

In an aspect of the present invention, a binder for a battery, such as lithium ion battery, comprises the bio-based copolymer as described hereinabove. In another aspect, an electrode is provided comprising the binder and an electrode active material.

In yet another aspect, a polymer electrolyte is provided, comprising the bio-based copolymer of the present invention, as described hereinabove and at least one salt. The polymer electrolyte can contain a mixture of two or more aforementioned bio-based copolymers with different structural units, different molecular weights, etc. The polymer electrolyte may also contain one or more types of polymers other than the bio-based copolymers described hereinabove. In one embodiment, the polymer electrolyte is solid (i.e., solid at room temperature). In another embodiment, the polymer electrolyte is essentially free or free of any volatile substances, such as organic solvents.

The at least one salt may include at least one lithium salt. Any suitable salt may be used, including but not limited to, LiBr, LiCl, $LiClO_4$, $LiPF_6$, $LiAsF_6$, $LiSbF_6$, $LiBF_4$, $LiCF_3SO_3$, $LiN(FSO_2)_2$, $LiN(CF_3SO_2)_2$, $LiN(C_2F_5SO_2)_2$, $LiC_6F_3N_4$, $LiC(CF_3SO_2)_3$, $Li_2B_{10}Cl_{10}$, $LiB(OCH_3)_4$, $LiB(C_2O_4)_2$, $LiB(CN)_4$, $LiBC_2O_4F_2$, $LiB(C_3O_4F)_2$, lithium acetate, and $LiAlCl_4$.

The quantity added of the electrolyte salt may typically be within a range from 0.005 to 80 mol %, e.g., from 0.01 to 50 mol %, relative to the quantity of (oligo-oxyethylene) units within the bio-based copolymer. Where the salt is a lithium salt, the molar ratio of [oxygen atoms in the (oligo-oxyethylene) units in the bio-based copolymer]:[Li] may be, for example from 1:1 to 100:1. In one embodiment, the molar ratio of oxygen atoms in the [(oligo-oxyethylene) units in the bio-based copolymer]:[Li] is 20:1.

In an embodiment, the aforementioned polymer electrolyte has conductivity in the range of $10^{-10}$-$10^{-1}$ or $10^{-9}$-$10^{-2}$ or $10^{-8}$-$10^{-3}$ S/cm.

In another embodiment, the aforementioned binder has conductivity in the range of $10^{-10}$-$10^{-1}$ or $10^{-9}$-$10^{-2}$ or $10^{-8}$-$10^{-3}$ S/cm.

A polymer electrolyte of the present invention can be produced by combining and mixing (complexing) an electrolyte salt with an aforementioned bio-based copolymer. There are no particular restrictions on the method used for this process, and suitable methods include a method in which the bio-based copolymer and the electrolyte salt are dissolved in a suitable solvent such as tetrahydrofuran, methyl ethyl ketone, acetonitrile, ethanol, or dimethylformamide (with the solvent later being removed), and a method in which the bio-based copolymer and the electrolyte salt are mixed together mechanically, either at room temperature or under heat.

Molding the aforementioned solid polymer electrolyte into sheet, membrane, film or other form may be performed using any of the techniques known in the polymer electrolyte art. For example, a sheet-like solid polymer electrolyte can be produced by any of a variety of coating techniques including roll coating, curtain coating, spin coating, dipping, or casting, and using one of these techniques, a film of the solid polymer electrolyte is formed on the surface of a substrate, and the substrate can be subsequently removed to yield the solid polymer electrolyte sheet as necessary.

Also, provided herein is an electrochemical device, in accordance with various embodiments of the present invention, the electrochemical device comprising an electrode in electrical contact with the aforementioned polymer electrolyte, wherein at least one of the electrode and the polymer electrolyte comprises the bio-based copolymer of the present invention, as disclosed herein above. In one embodiment of the electrochemical device, only the electrode comprises the bio-based copolymer of the present invention. In another embodiment of the electrochemical device, only the polymer electrolyte comprises the bio-based copolymer of the present invention. In yet another embodiment of the electrochemical device, both the electrode and the polymer electrolyte comprise the bio-based copolymer of the present invention.

In one embodiment, the electrochemical cell, such as a lithium ion battery comprises an electrode in electrical contact with the aforementioned polymer electrolyte, wherein at least one of the electrode and the polymer electrolyte comprises the bio-based copolymer of the present invention, for example a diblock bio-based copolymer, poly(guaiacyl methacrylate)-b-poly(oligo-oxyethylene methacrylate) (P(GMA)-b-P(OEM) having the following structure (VI) or a triblock bio-based copolymer, poly(guaiacyl methacrylate)-b-poly(oligo-oxyethylene methacrylate)-b-poly(guaiacyl methacrylate) (P(GMA)-b-P(OEM)-b-P(GMA)) having the following structure (VII):

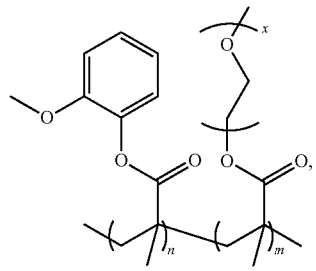

(VI)

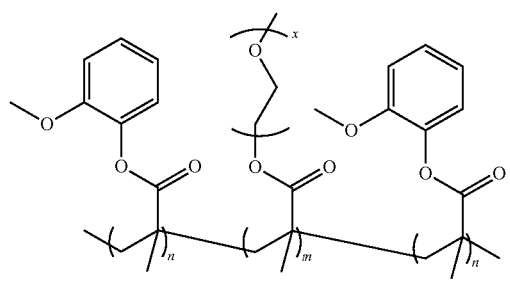

(VII)

wherein x is in the range of 2-1000, or 4-20, or 6-12; n in the range of 10-500, or 15-100, or 20-50; and m in the range of 10-1000, or 15-200, or 20-50.

Depending on the ratio of n and m as well as the overall degree of polymerization (n+m in the case of a diblock or 2n+m in the case of a triblock), nanoscale morphologies including spheres, hexagonally-packed cylinders, double gyroid, or lamellae are achievable. Domain spacing of the bio-based copolymer is in the range of 5-100 nm, or 10-80 nm, or 20-50 nm.

To use the bio-based copolymer as a binder, the electrode active material, conductive carbon, and the bio-based copolymer are thoroughly mixed in n-methyl-2-pyrrolidone to prepare a slurry. The slurry is spread on a copper foil and dried at 150° C. overnight.

An Article Comprising an Adhesive Composition

In an aspect of the invention, an article is provided comprising an adhesive composition adhesively disposed over a substrate. In an embodiment, the adhesive composition comprises a bio-based block copolymer in accordance with the invention and optionally at least one additive. The bio-based block copolymer may include at least one bio-based polymeric block comprising, in polymerized form, at least one polymerizable bio-based monomer having a structure corresponding to formula (II):

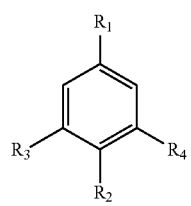

(II)

$R_1$ can be hydrogen, methyl, ethyl, n-propyl, i-propyl, or propylene. $R_2$ can be a substituent comprised of at least one polymerizable functional group that is an ethylenically unsaturated functional group, as disclosed hereinabove. $R_3$ and $R_4$ can both be H, or can both be methoxy, or can be hydrogen and methoxy. The ethylenically unsaturated functional group has been polymerized to form at least one bio-based polymeric block. The bio-based block copolymer also includes a co-monomer-based polymeric block comprising, in polymerized form, at least one polymerizable co-monomer other than a polymerizable bio-based monomer. Any suitable polymerizable co-monomer may be used including, but not limited to, an alkyl [meth]acrylate. In an embodiment, the at least one polymerizable co-monomer includes an alkyl [meth]acrylate, where the alkyl group may be selected from the group consisting of C1 to $C_{18}$ alkyl groups. In an embodiment, the alkyl group is a butyl group. In an embodiment, $R_1$ is a propyl group.

In some embodiments, the block polymer may be a triblock bio-based copolymer comprising the alkyl [meth]acrylate as the polymerizable co-monomer in polymerized form for the midblock and the at least one polymerizable bio-based monomer in polymerized form as one or both of the glassy end blocks. An exemplary triblock bio-based copolymer can be poly(4-propylsyringyl acrylate-b-butyl acrylate-b-4-propylsyringyl acrylate) having the following structure (V):

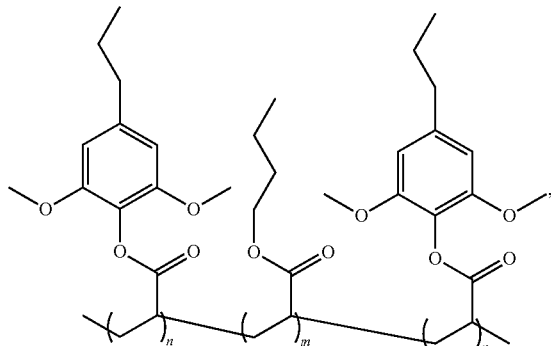

(V)

and wherein n is in the range of 10-500, or 15-100, or 20-50; and m in the range of 10-1000, or 15-200, or 20-50

In an embodiment, the adhesive composition can be a pressure sensitive adhesive composition.

In another embodiment, one or more additives are present in the adhesive composition, in addition to the bio-based copolymer, and may be selected from the group consisting of tackifiers, plasticizers, viscosity modifiers, photoluminescent agent, anti-counterfeit and UV-reactive additives, dyes/pigments, anti-static materials, surfactants, and lubricants. In another embodiment, the adhesive composition is free of tackifier.

The article of the present invention may include any suitable substrate, including but not limited to, a polymeric film, a paper label, a tape backing, a graphic article, a plastic article, a metal article, a wound dressing, a protection film or tape, or a release liner.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the composition or process. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

EXAMPLES

General Procedure of Lignocellulosic Biomass Depolymerization, Purification, and Characterization.

FIG. 1 shows a general reaction scheme for depolymerizing poplar wood in methanol with a commercially available Ru/C catalyst, which is effective and selective to C—O bonds cleavage.[27,40]

In particular, poplar wood powder (1 g, particle size <0.5 mm), methanol (20 mL), and catalyst (5 wt % Ru/C, Sigma-Aldrich, 100 mg) were added to a 50 mL high-pressure Parr reactor. The reactor was purged with $H_2$ three times and then pressurized with $H_2$ to a pressure of 40 bar. The reactor was heated to 250° C. and held for 15 h while stirring. After the reaction was completed, the reactor was cooled to room temperature with an external flow of compressed air. The solution containing aromatic monomers was separated from the resultant slurry by filtration. The solid (cellulose, catalyst) was washed with methanol (10 mL, 3 times), and the solution was combined with the previous methanol solution. Methanol was removed using a rotary evaporator at 60° C., and the residue was extracted with cyclohexane (10 mL, 3 times) to obtain pure 4-propylsyringol (4pS) and 4-propylguaiacol (4pG) mixture in the cyclohexane phase (light brown color). The aromatic monomers from the poplar wood feedstock were analyzed before and after the cyclohexane extraction on an Agilent 7890B series gas chromatograph (GC) equipped with a HP5 capillary column and an Agilent 5977A series mass spectroscopy detector (FIG. 1). The following operating conditions were used: injection temperature of 250° C., a column temperature program of 50° C. (held for 1 min), heating ramp to 300° C. at 15° C. $min^{-1}$, and then 300° C. (held for 7 min). The detector temperature was 290° C.

Figure 2A:
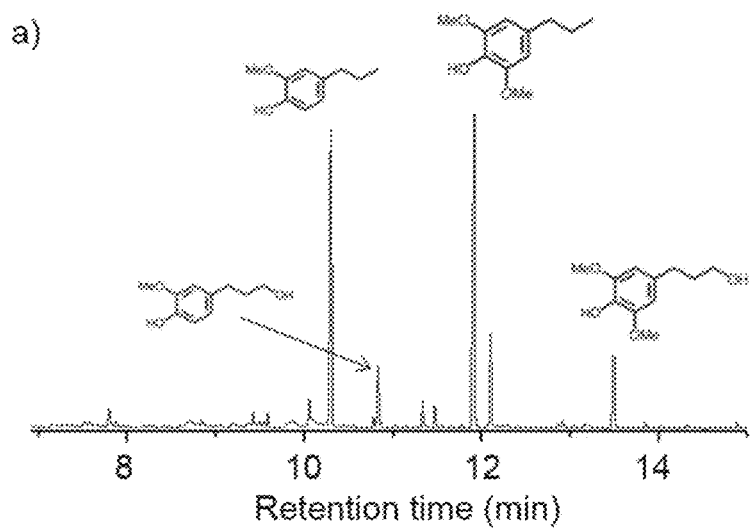
FIG. 2A shows gas chromatography (GC) trace of raw biomass depolymerization products before extraction with cyclohexane.
Figure 2B:
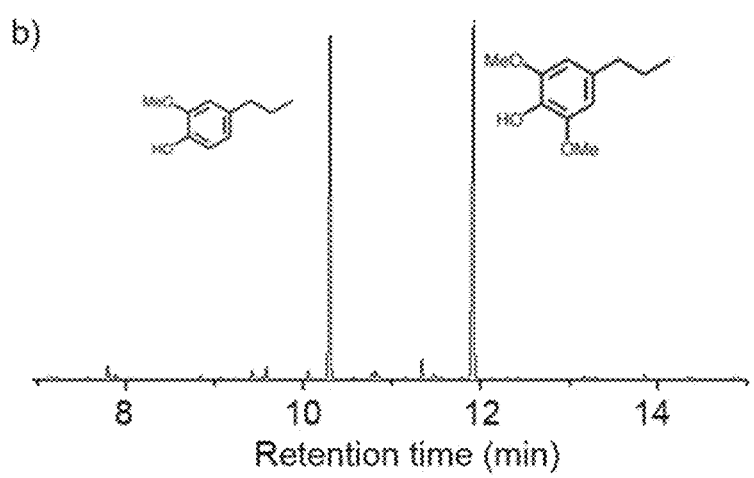
FIG. 2B shows gas chromatography (GC) trace of raw biomass depolymerization products after extraction with cyclohexane.

FIG. 2A shows that two prominent monophenolic compounds, 4-propylsyringol (4pS) and 4-propylguaiacol (4pG), were collected, along with small portions of other dihydroxyl-containing components. FIG. 2B shows that following a simple extraction with cyclohexane, high purity monophenolic compounds, 4pS and 4pG, were obtained with relative mass fractions of 0.6 and 0.4, respectively, at a total yield of 10 wt % on the basis of weight of dry poplar wood. The removal of the dihydroxyl species is critical to prevent the formation of a crosslinked network during the polymerization process. 4pS and 4pG then were efficiently functionalized with either acrylate or methacrylate groups, followed by polymerization via a scalable RAFT polymerization approach, as described below.

Synthesis and Characterization of Lignin-Based Monomers: 4-Propylsyringyl Acrylate (4pSA), 4-Propylguaiacyl Acrylate (4pGA), 4-Propylsyringyl Methacrylate (4pSMA), and 4-Propylguaiacyl Methacrylate (4pGMA)

The aromatic monomer mixture, comprising 4pS and 4pG, was acrylated with acryloyl chloride for the synthesis of acrylates and methacryloyl chloride for the synthesis of methacrylates, following a procedure adapted from the disclosure of the following article authored by the inventors, is hereby incorporated by reference in its entirety for all purposes: Wang et. al., "Effect of methoxy substituent position on thermal properties and solvent resistance of lignin-inspired poly(dimethoxyphenyl methacrylate)s," ACS Macro Letters 2017, 6 (8), 802-807.

The aromatic monomers and triethylamine (1.2 mol eq, Fisher Scientific, 99%) were dissolved in dichloromethane (DCM, anhydrous, Fisher Scientific) in a three-neck round bottom flask. The mixture was sparged with argon for 15 min while the flask was immersed in an ice-water bath. A solution of acryloyl chloride (1.2 mol eq, Sigma Aldrich, 97%) in DCM was added drop wise using a constant pressure dropper. The reaction was left to proceed overnight, after which, a white precipitant was filtered by vacuum filtration and discarded. The DCM permeate phase was washed consecutively with solutions of saturated sodium bicarbonate, 1.0 M NaOH (twice), 1.0 M HCl, and deionized water. DCM was removed by rotary evaporation, and the monomers were further purified by flash chromatography using silica gel (Standard Grade, 230×400 mesh, 60 Å) with ethyl acetate/hexanes mixture as an eluent (ethyl acetate volume fraction gradually increased from 0% to 10%). Two pure products, 4-propylsyringyl acrylate (4pSA) and 4-propylguaiacyl acrylate (4pGA), were obtained.

$^1$H NMR (CDCl$_3$, 600 MHz, δ) for:

4pSA: 6.62 (1H, d), 6.44 (2H, aromatic, s), 6.40 (1H, q), 6.00 (1H, d), 3.80 (6H, s), 2.56 (2H, t), 1.65 (2H, m), 0.97 (3H, t); and 4pGA: 6.96 (1H, d), 6.79 (1H, d), 6.76 (1H, d), 6.60 (1H, d), 6.35 (1H, q), 5.99 (1H, d), 3.81 (3H, s), 2.58 (2H, t), 1.65 (2H, m), 0.96 (3H, t).

Aromatic monomers (4pS and 4pG) also were methacrylated using the same procedure, except substituting methacryloyl chloride (1.2 mol eq, Alfa Aesar, 97%) for acryloyl chloride. Two products, 4-propylsyringyl methacrylate (4pSMA) and 4-propylguaiacyl methacrylate (4pGMA) were collected.

$^1$H NMR (CDCl$_3$, 600 MHz, δ) for:

4pSMA: 6.45 (2H, s), 6.40 (1H, s), 5.76 (1H, t), 3.82 (6H, s), 2.58 (2H, t), 2.10 (3H, s), 1.65 (2H, m), 0.97 (3H, t); and 4pGMA: 6.95 (1H, d), 6.78 (1H, d), 6.76 (1H, d), 6.34 (1H, s), 5.72 (1H, t), 3.81 (3H, s), 2.57 (2H, t), 2.06 (3H, s), 1.65 (2H, m), 0.96 (3H, t).

Synthesis of Lignin-Based Polymers: Poly(4-Propylsyringyl Acrylate) (P(4pSA)), Poly(4-Propylguaiacyl Acrylate) (P(4pGA)), Poly(4-Propylsyringyl Methacrylate) (P(4pSMA)), and Poly(4-Propylguaiacyl Methacrylate) (P(4pGMA))

Poly(4pSA) and poly(4pGA) were synthesized by RAFT polymerization, using a procedure described in the literature.[18] The initiator, 2,2'-azobisisobutyronitrile (AIBN, Sigma-Aldrich, 98%), was recrystallized twice from methanol prior to use. The chain transfer agent (CTA), 3,5-bis(2-dodecyl-thiocarbonothioylthio-1-oxopropoxy)benzoic acid (BTCBA, Sigma Aldrich, 98%), was used as received. The polymerization solvent, anisole (Sigma-Aldrich, ≥99.7%) with 5 wt % N,N-dimethylformamide (DMF, Sigma-Aldrich, ≥99.9%), was prepared and stored on molecular sieves to minimize water content.

The monomer (4pSA or 4pSGA), BTCBA and AIBN were dissolved in the polymerization solvent and transferred to a pressure vessel. The reaction mixture was degassed by three freeze-pump-thaw cycles, backfilled with argon to a pressure of 3 psi, sealed with a stopcock, and immersed in an oil bath (70° C.) with vigorous stirring. The reaction was quenched at a predetermined time (typical reaction time was 6-7 h) by immersing the pressure vessel in liquid nitrogen. Tetrahydrofuran (THF, Fisher Scientific, certified) was added to the mixture, and the polymer was purified by precipitating into excess hexanes at least two times to ensure no monomer remained (confirmed by 1H NMR spectroscopy).

The same procedure was employed in the synthesis of P(4pSMA) and P(4pGMA), except that 2-cyano-2-propyl benzodithioate (CPB, STREM Chemicals, 97%) was utilized as the CTA.

Synthesis of Bio-Based Diblock Copolymer: Poly (4-Propylsyringyl Methacrylate-Co-4-Propylguaiacyl Methacrylate) P(4pSMA-Co-4pGMA)

A bio-based copolymer of 4pSMA and 4pGMA (poly(4pSMA-co-4pGMA)) also was synthesized to demonstrate the feasibility of making polymers from the original biomass mixture, without fractionation into individual components. The monomer ratio of 4pSMA/4pGMA (0.60/0.40) and the segment content in the polymer (0.58/0.42, as determined via $^1$H NMR spectroscopy) were consistent, suggesting a random incorporation of each substituent in the polymer backbone.

The bio-based copolymer (poly(4pSMA-co-4pGMA) was made following the procedure described hereinabove for the synthesis of poly(4pSA) and poly(4pGA), except that a mixture of 4pSMA and 4pGMA at a ratio of 0.6/0.4 was fed instead of the single monomers (4pSA or 4pGA).

The characteristics of the bio-based polymers derived from lignin-based monomers: polymers, poly(4-propylsyringyl acrylate) (P4pSA), poly(4-propylguaiacyl acrylate) (P4pGA), poly(4-propylsyringyl methacrylate) (P4pSMA), and poly(4-propylguaiacyl methacrylate) (P4pGMA), are summarized in Table 1.

TABLE 1

Characteristics of lignin-derived polymers

| Polymer | $M_n^a$ (kg mol$^{-1}$) | $D^b$ | $T_g^c$ (° C.) |
|---|---|---|---|
| P(4pSA) | 19.1 | 1.44 | 98 |
| P(4pSMA) | 30.4 | 1.16 | 169 |
| P(4pGA) | 29.6 | 1.29 | 56 |
| P(4pGMA) | 12.4 | 1.29 | 80 |
| P(4pSMA-co-4pGMA) (0.58/0.42)$^d$ | 26.7 | 1.26 | 135 |

$^a$Number-average molecular weight, determined by size-exclusive chromatography (SEC);
$^b$Dispersity, determined by SEC;
$^c$Determined by differential scanning calorimetry (DSC);
$^d$A mixture of 4pSMA and 4pGMA was fed, and the numbers denote the composition of 4pSMA and 4pGMA (mol/mol) in the resulting bio-based copolymer.

As summarized in Table 1, the glass transition temperatures ($T_g$)s of P(4pSA) (98° C.) and P(4pSMA) (169° C.) were attractive relative to polystyrene (PS, $T_g$~100° C.) and PMMA ($T_g$~110° C.), as $T_g$s of lignin-derived polymers are tunable and can be significantly higher than polystyrene, which provides greater thermal stability. It should be noted that the $T_g$s of P(4pGA) (56° C.) and P(4pGMA) (80° C.) with one methoxy group at the ortho position were lower than those of P(4pSA) and P(4pSMA). Without wishing to be bound by any particular theory, it is believed that the existence of two ortho methoxy groups constrained rotation of the pendant groups and raised the $T_g$s of the dimethoxy-based polymers.

The bio-based copolymer poly(4pSMA-co-4pGMA) had a $T_g$ of 135° C., which was close to that estimated for a random bio-based copolymer of 4pSMA and 4pGMA on the basis of the Flory-Fox equation (~127° C.).

The thermal behavior of these lignin-based polymers, copolymers and block copolymers, especially the desirable glass transition temperatures, provides an initial indication of their utility in the PSA materials.

Synthesis of Bio-Based Triblock Copolymer: Poly (4-Propylsyringyl Acrylate-b-Butyl Acrylate-b-4-Propylsyringyl Acrylate) (P(4pSA-b-BA-b-4pSA)) (Also Referred Herein as SaBSa)

To demonstrate the ease of producing model consumer products directly from raw biomass depolymerization products, a triblock polymer was synthesized with P(4pSA) as the glassy end blocks and poly(n-butyl acrylate) (PBA) as the midblock, generating poly(4pSA-b-BA-b-4pSA)

In particular, the triblock bio-based copolymer was synthesized with P(4pSA) as the glassy end blocks and PBA as the midblock, generating (poly(4-propylsyringyl acrylate-co-butyl acrylate-co-4-propylsyringyl acrylate)) (P(4pSA-b-BA-b-4pSA)) to demonstrate the ease of producing model consumer products directly from raw biomass depolymerization products.

The triblock bio-based copolymer P(4pSA-b-BA-b-4pSA) was synthesized in a two-step RAFT polymerization, using BTCBA as the CTA. PBA was synthesized first, following the general procedure described hereinabove, except that the polymer was precipitated into cold methanol. Then, PBA was chain-extended with the monomer 4pSA to make the P(4pSA-b-BA-b-4pSA) triblock bio-based copolymer. P(4pSA-b-BA-b-4pSA) was isolated by precipitation in cold methanol three times to remove unreacted 4pSA and dried in vacuum for 2 days at 40° C.

Figure 3:
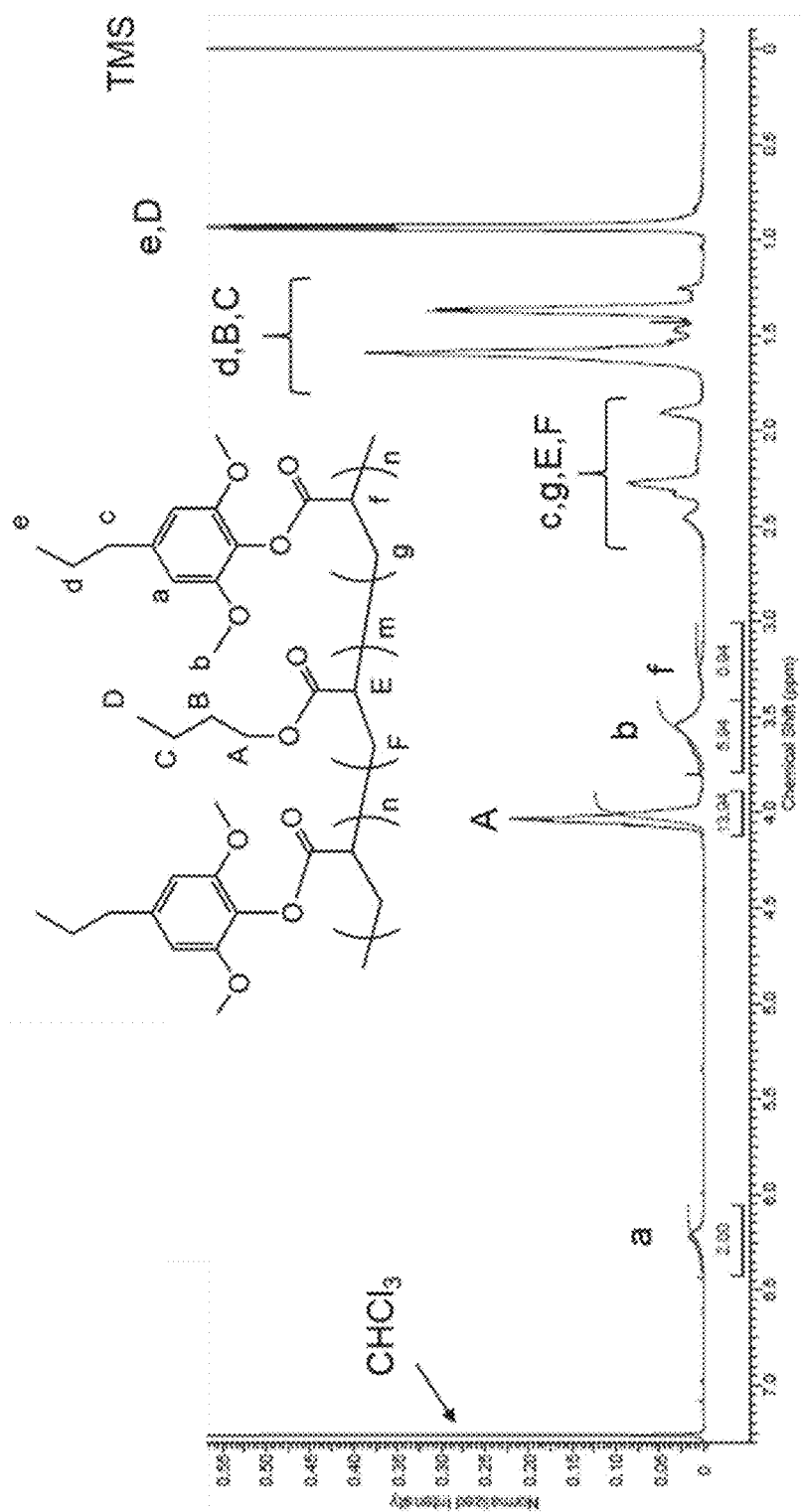
FIG. 3 shows $^1$H NMR spectrum of SaBSa in chloroform-d (with TMS as an internal standard).

$^1$H NMR spectrum of P(4pSA-b-BA-b-4pSA) with TMS as an internal standard (CDCl$_3$, 600 MHz, δ) is shown in FIG. 3. The weight percentage of the 4pSA blocks was calculated from the $^1$H NMR data, as follows:

$$\frac{\text{area}(a) \times \text{MW}(4pSA)}{\text{area}(a) \times \text{MW}(4pSA) + \text{area}(A) \times \text{MW}(n-BA)} \times 100\% =$$

$$\frac{2 \times 250.29}{2 \times 250.29 + 13.94 \times 128.17} \times 100\% = 22\%$$

where the area(a) and area(A) refer to the area under the peaks labeled a and A, respectively, in FIG. 3.

Figure 4:
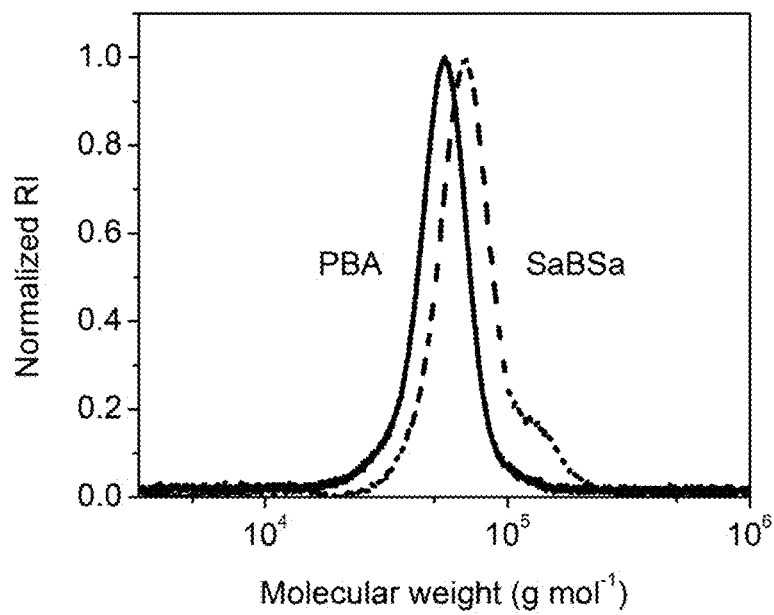
FIG. 4 shows size exclusion chromatography (SEC) traces of poly(butyl acrylate) (PBA) (solid line, M$_n$=49.7 kg mol$^{-1}$, Đ=1.11) and poly(4-propylsyringyl acrylate-b-butyl acrylate-b-4-propylsyringyl acrylate) (SaBSa) (dashed line, M$_n$=66.4 kg mol$^{-1}$, Đ=1.15). RI denotes refractive index detector response.

Comparative Analysis of Bio-Based Triblock Copolymer (P(4pSA-b-BA-b-4pSA)) of the Present Invention with a Commercially Available Triblock Copolymer (P(MMA-b-BA-b-MMA)) for Use in Pressure Sensitive Adhesive (PSA) Applications FIG. 4 shows the SEC chromatograms of PBA and P(4pSA-b-BA-b-4pSA). The clean shift in molecular weight from before (M$_n$=49.7 kg mol$^{-1}$, Đ=1.11) to after addition of the P(4pSA) end blocks clearly indicates the ability to chain extend using the biomass-derived monomers, while retaining substantial control over the polymerization. The final P(4pSA-b-BA-b-4pSA) triblock bio-based copolymer had a M$_n$ of 66.4 kg mol$^{-1}$, a Đ of 1.15, and a P(4pSA) weight percentage of 22%. These macromolecular characteristics were targeted to approximate a commercial poly(MMA-b-BA-b-MMA) (P(MMA-b-BA-b-MMA Kurarity LA2140e, M$_n$=66.9 kg mol$^{-1}$, Đ=1.12, 23 wt % PMMA) produced by Kuraray Co., Ltd for use in PSAs.

Figure 5:
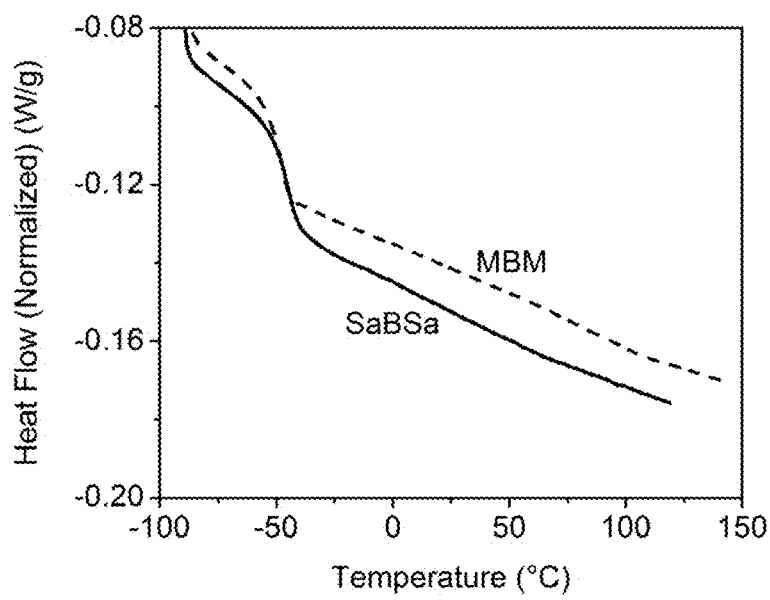
FIG. 5 shows differential scanning calorimetry (DSC) traces of the second heating (exotherm up, heating rate=5° C. min$^{-1}$ under continuous N$_2$ flow at 50 mL mi$^{-1}$) for SaBSa [solid line, M$_n$=66.4 kg mol$^{-1}$, 22 wt % P4pSA] and poly(methyl methacrylate-b-butyl acrylate-b-methyl methacrylate) (MBM) [dashed line, M$_n$=66.9 kg mol$^{-1}$, 23 wt % poly(methyl methacrylate) (PMMA)].

The thermal behavior and phase separation characteristics of P(4pSA-b-BA-b-4pSA) and P(MMA-b-BA-b-MMA) were compared by measuring T$_g$s and size-scales of microphase separation via DSC and small-angle X-ray scattering (SAXS), respectively. T$_g$s corresponding to the PBA-rich domains were detected at −45° C. (P(4pSA-b-BA-b-4pSA)) and −49° C. (P(MMA-b-BA-b-MMA)), as shown in FIG. 5. No clear transition of P(4pSA) (~98° C.) or P(MMA) (~110° C.) was found. Without wishing to be bound by any particular theory, it is believed that this is likely due to the low weight fraction of the end block in each polymer (~11 wt % for each end block). However, the similarity of T$_g$ of PBA block in the triblock bio-based copolymer to that of PBA homopolymer is suggestive of block immiscibility and microphase separation. Nanoscale phase separation in the lignin-based P(4pSA-b-BA-b-4pSA) triblock bio-based copolymer was confirmed by SAXS. A principal scattering peak (q*) at 0.030 Å$^{-1}$, corresponding to a domain spacing (D*=2π/q*) of ~21 nm, was clearly visible in the 1-D azimuthally integrated SAXS data, as shown in FIGS. 6A and 6B. A similar scattering pattern also was obtained for P(MMA-b-BA-b-MMA) (FIGS. 6C and 6D), which suggested a domain spacing of ~20 nm.

Figure 7:
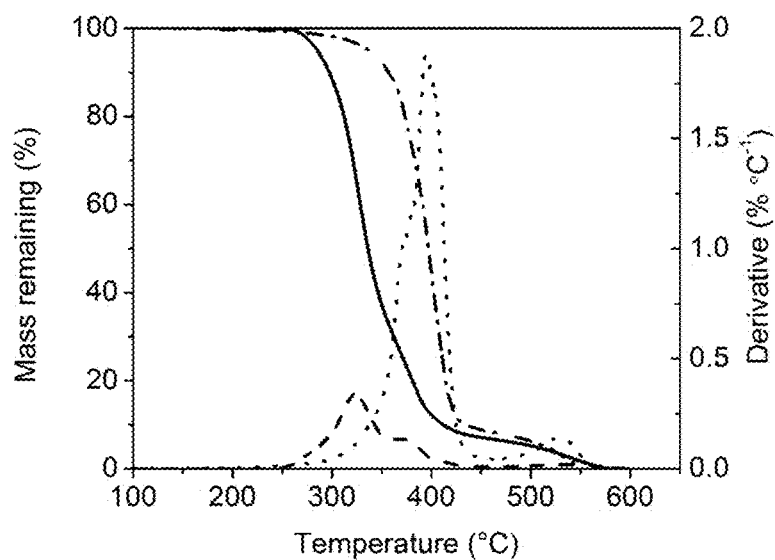
FIG. 7 shows a) mass remaining as a function of temperature for SaBSa (solid line, M$_n$=66.4 kg mol$^{-1}$, 22 wt % P4pSA) and MBM (dash-dotted line, M$_n$=66.9 kg mol$^{-1}$, 23 wt % PMMA); b) the first derivative of mass remaining curve a) as a function of temperature for SaBSa (dashed line, M$_n$=66.4 kg mol$^{-1}$, 22 wt % P4pSA) and MBM (dotted line, M$_n$=66.9 kg mol$^{-1}$, 23 wt % PMMA). The heating rate was 10° C. min$^{-1}$ under air flow.

The overall thermal stability of P(4pSA-b-BA-b-4pSA) was evaluated by thermogravimetric analysis (TGA), and the bio-derived triblock exhibited excellent thermal stability. P(4pSA-b-BA-b-4pSA) was thermally stable up to 337° C. under air (the temperature at which the weight of the polymer was reduced by 5%), as shown in FIG. 7. In comparison, the thermal stability of P(MMA-b-BA-b-MMA) characterized in air flow, was much lower, with a 5% degradation temperature of 285° C., as shown in FIG. 7. Furthermore, when comparing P(4pSA-b-BA-b-4pSA) to other model bio-inspired PSAs reported in the literature, the lignin-derived materials herein have thermal degradation temperatures in air that are at least 30° C. higher than acrylate-functionalized glucose, acrylate-functionalized isosorbide, and polyester-based systems,[38-39,42] providing a much larger temperature window for processing.

While the thermal parameters are important, adhesion performance is critical in evaluating the potential of materials as PSAs. Herein, three tests were performed to assess adhesive properties: a 180° peel test (ASTM D3330, width 12.7 mm), a loop tack force test (ASTM D6195, width 12.7 mm), and a shear strength test (ASTM D3654, contact area of 12.7 mm×12.7 mm). The 180° peel test determines the force needed to tear a strip off the adherend at a constant speed; the loop tack force test measures the bonding strength that forms instantly between adhesive and adherend when they are brought into contact; and the shear strength test probes the resistance of the adhesive to creep under an applied load. In addition to the above test, the mode of PSA failure qualitatively evaluated as either adhesive (interfacial failure with no residue left on the substrate) or cohesive (failure within the adhesive layer itself, leaving residue on the substrate), noting that adhesive failure is more desirable for removable PSAs, while cohesive failure is more favorable for permanent PSAs.[28,39]

The neat P(4pSA-b-BA-b-4pSA) triblock bio-based copolymers exhibited excellent adhesion properties, without the addition of any tackifiers or other additives. 180° peel force and loop tack force data (stainless steel as the adherend) of P(4pSA-b-BA-b-4pSA) are summarized below in Table 2. Also, data for P(MMA-b-BA-b-MMA), Scotch® Magic™ Tape, and Fisherbrand™ Labeling Tape are summarized for comparison. All four samples had adhesive failure, leaving no residue on the adherend.

In the shear test, a 500 g weight was suspended from a SaBSa polymer strip adhered to stainless steel plate, and the time for the SaBSa to detach from the adherend was recorded and summarized in Table 2. Three samples of P(4pSA-b-BA-b-4pSA) were tested, with a range of failure time of 570-810 min. The shear resistance of P(4pSA-b-BA-b-4pSA) was better than commercial duct tape, electrical tape, and Post-It® notes, but not as good as Scotch® Tape and Paper tape. The peel and loop tack forces of biomass-derived P(4pSA-b-BA-b-4pSA) also were as good as or better than those reported in potentially bio-based polyesters-based PSAs (with the addition of tackifier) and acrylic PSAs with glucose or isosorbide components (no addition of tackifier).[38-39,42-44] These comparisons reveal that lignocellulosic biomass-derived P(4pSA-b-BA-b-

4pSA) polymers are extremely promising for PSA applications, without the addition of tackifiers or any other additives.

TABLE 2

Adhesion Tests

| | Range (Average) of 180° peel force, N cm$^{-1}$ | Average loop track force, N cm$^{-1}$ | shear test (Time for failure), min |
|---|---|---|---|
| P(4pSA-b-BA-b-4pSA) | 2-4 (3.1) | 2.2 | 570-810 |
| P(MMA-b-BA-b-MMA) | 0.2-0.5 | unable to bind width the adherend | |
| Scotch ® Magic ™ Tape | 1.7-2.0 | 1.4 | |
| Fisherbrand ™ Labeling Tape | 3.5-5 | 3.9 | |
| Commercial duct tape (width 25 mm) | | | 200 |
| electrical tape (width 20 mm) | | | 500 |
| Post-it ® notes (width 16 mm) | | | <0.5 |
| Scotch ® Tape (width 20 mm | | | >10,000 |
| Paper Tape (width 25 mm) | | | 1400 |

Testing Methods
Characterization of Polymers.

The number-average molecular weight ($M_n$) and dispersity (Đ) of the synthesized polymers and (P(MMA-b-BA-b-MMA) were obtained using a Viscotek VE2001 size exclusion chromatography (SEC) instrument with THF (Optima) as the eluent (1.0 mL min$^{-1}$) and polystyrene standards (1.78-205 kg mol$^{-1}$) as the reference.

Glass transition temperatures ($T_g$)s of all polymers were determined using a differential scanning calorimeter (DSC, Discovery Series, TA Instruments). The DSC was calibrated using an indium standard. Polymer sample (2-5 mg) was loaded into an aluminum pan and hermetically sealed in air. A heating-cooling-heating cycle was carried out at a rate of 5° C. min$^{-1}$ under continuous N$_2$ flow (50 mL min$^{-1}$). For P(4pSA-b-BA-b-4pSA)), the sample was first heated from 35° C. to 120° C., held at 120° C. for 2 min, cooled down to −90° C., held at −90° C. for 2 min, and ramped to 120° C. The procedure for P(MMA-b-BA-b-MMA, Kurarity LA2140e, Kuraray Co. Ltd.) was the same except that the experimental temperature window was −90° C. to 150° C. The $T_g$ was determined as the midpoint of the inflection in the second heating.

The thermal degradation behavior of P(4pSA-b-BA-b-4pSA)) was characterized using thermogravimetric analysis (TGA, Discovery Series, TA Instruments). 9-11 mg of P(4pSA-b-BA-b-4pSA)) triblock bio-based copolymer was loaded into a 100 μL platinum pan and heated under continuous airflow (50 mL min$^{-1}$ sample purge, 20 mL min$^{-1}$ balance purge). The sample was heated at 20° C. min$^{-1}$ to 110° C., annealed at 110° C. for 15 min to remove possible residual water, cooled at 10° C. min$^{-1}$ to 50° C., held at 50° C. for 1 min, and heated at 10° C. min$^{-1}$ to 600° C.

Tensile testing on lignin-based polymers was performed using dog-bone-shaped testing bars (following ASTM D638, bar type 5, 5.3 mm gauge width, 0.8 mm thickness) that were prepared by compression molding into a Teflon PTFE sheet (McMaster Carr) on a PHI Hotpress at 200° C., with an applied load of 9000 lb. Tensile testing was performed with a RSA-G2 Solids Analyzer (TA Instruments) in tension mode. The lower grip was stationary, and the upper grip was raised at a speed of 10 mm min$^{-1}$ to obtain tensile strength and elongation at break of P(4pSA-b-BA-b-4pSA)) at room temperature. The measurement was repeated with four test specimens. Tensile testing on P(MMA-b-BA-b-MMA) also was performed for comparison, except that the testing specimens were prepared with an aluminum mold, and the pressing temperature was 220° C.

The micro-phase separation characteristics of P(4pSA-b-BA-b-4pSA)) and P(MMA-b-BA-b-MMA) were probed by small-angle X-ray scattering (SAXS) (Rigaku SAXS instrument at the University of Delaware). The wavelength of the beam was 0.154 nm, and the sample to detector distance was 2 m. The 2D scattering patterns were azimuthally integrated to a 1D profile of intensity [I(q)] vs. scattering vector q, q=4π sin(θ/2)/λ (θ is the scattering angle, λ is the wavelength).

Testing Methods for Adhesive Compositions
Adhesion Testing.

Polymer films were prepared by casting polymer solution onto a 50 μm thick sheet of PET (McMaster Carr). 30 wt % P(4pSA-b-BA-b-4pSA)) or (P(MMA-b-BA-b-MMA) solution was made by dissolving 100 mg P(4pSA-b-BA-b-4pSA)) or (P(MMA-b-BA-b-MMA) into 230 mg o-xylene (Sigma Aldrich, 97%). Polymer films with ~20 μm thickness were prepared by casting the solution onto PET sheet using a homebuilt flow coater[45] at a speed of 10 mm s$^{-1}$ with a blade width of 12.7 mm and a gap height of 100 μm. The films were dried under ambient conditions for 24 h before adhesion testing. Mirror-like stainless-steel plate (McMaster Carr) was used as the adhered.

180° Peel Test in Accordance with ASTM D3330:

A P(4pSA-b-BA-b-4pSA)) film strip (width 12.7 mm) was adhered to the stainless-steel plate using a 4.5 lb hand roller. The stripes were mounted to a RSA-G2 Solids Analyzer and tested at a peel rate of 5 mm/s. The peel force was averaged across the plateau in force for four samples.

Loop Tack Test in Accordance with ASTM D6195:

A P(4pSA-b-BA-b-4pSA)) film strip (width 12.7 mm) was formed into a teardrop-shaped loop and mounted to the upper grip of the RSA-G2 Solids Analyzer. The loop then was lowered onto the stainless-steel plate mounted to the lower grip. The contact length of the strip was ~30 mm. The upper grip was raised at a speed of 5 mm s$^{-1}$ until the strip detached from the adherend. The maximum force was recorded as the tack force, and the average of three samples was reported.

Shear Test in Accordance with ASTM D3654:

The film strip was adhered to a stainless-steel plate with a contact area of 12.7 mm×12.7 mm, using a 4.5 lb hand roller. A 500 g weight then was suspended from the strip, and the average time to failure of three samples was reported.

Copolymers Suitable for Use as Binders and Electrolytes

Synthesis and Characterization of Lignin-Based Monomer: Guaiacyl Methacrylate (GMA)

Guaiacol used in the present example was purchased from Acros, but according to various embodiments of the present invention, guaiacol could be sourced from biomass such as lignocellulosic biomass, as described hereinabove.

Guaiacyl methacrylate (GMA) synthesis was adapted from previously reported method by Wang, as disclosed hereinabove, and from the disclosure of the following article, incorporated herein in its entirety: Gargallo, L.; Hamidi, N.; Radic, D., Synthesis, Solution Properties and Chain Flexibility of Poly(2,6-Dimethylphenyl Methacrylate). Polymer 1990, 31 (5), 924-927 (hereinafter "Gargallo").

Guaiacol (Acros, 99+%, 1 mol) and triethylamine (Fisher Scientific, 99%, 1.2 mol) were dissolved in dichloromethane (Fisher Scientific) in a round-bottom flask and placed into an ice bath. The mixture was sparged with argon for 30 minutes before a solution of methacryloyl chloride (1.2 mol, Alfa Aesar, 97%) in DCM was added dropwise, and the mixture was allowed to react overnight. The product was washed with saturated sodium bicarbonate, 1.0 M NaOH, 1.0 M HCl, saturated NaCl, and deionized water; the solvent subsequently was removed by rotary evaporation. The monomer was further purified by flash chromatography with silica gel with ethyl acetate/hexanes mixtures and dried by rotary evaporation and on a vacuum line.

Synthesis of Lignin-Based Polymers: Poly(Guaiacyl Methacrylate) (P(GMA) or PGM)

Figure 8:
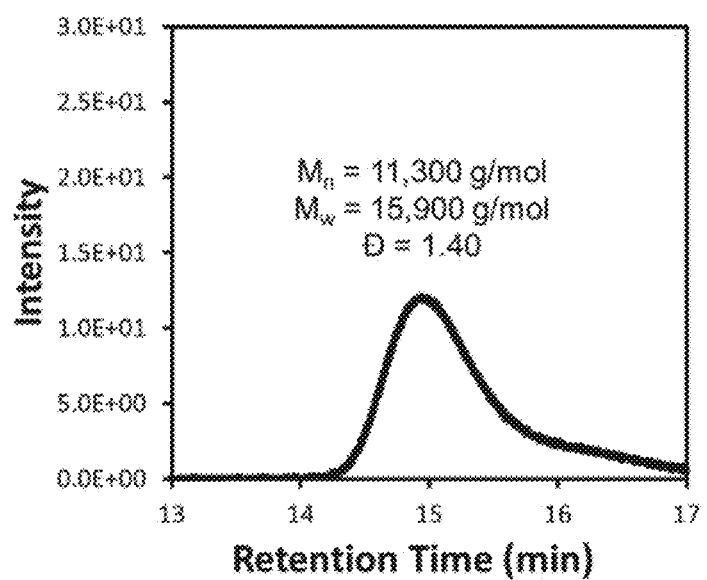
FIG. 8 shows gel permeation chromatography (GPC) trace of PGM.

Poly(guaiacyl methacrylate) was synthesized via activators regenerated by electron transfer (ARGET) ATRP. GMA (1 mol), $CuBr_2$ ($7.48 \times 10^{-4}$ mol, Aldrich, 99.999%), N,N,N', N'',N''-Pentamethyldiethylenetriamine (PMDETA, $7.48 \times 10^{-3}$ mol, Aldrich, 99%), tin(II) 2-ethylhexanoate ($7.48 \times 10^{-3}$ mol, Aldrich, 92.5%), and anisole (3.2 mol, Sigma-Aldrich, anhydrous, 99.7%) were added to a round-bottom flask and sparged with argon for 30 minutes. The reaction mixture was heated to 60° C., and degassed ethyl α-bromoisobutyrate (EBiB, $7.48 \times 10^{-3}$ mol, Aldrich, 98%) was added to the reaction mixture to initiate the polymerization. The reaction was tracked via $^1$H NMR spectroscopy and GPC in THF (>99%, optima, Fisher Scientific) of aliquots taken at 15, 30, and 60 minutes and was stopped at 90 minutes. Aliquots and final reaction mixture were precipitated in methanol to stop the reaction. The final polymer's GPC trace is shown in FIG. 8. Because only a single peak was observed in the GPC trace, it was determined that the ARGET ATRP was successful at controlling this polymerization with good molecular weight control and low dispersity.

Synthesis of Lignin-Based Diblock Copolymer: Poly(Guaiacyl Methacrylate)-b-Poly(Oligo-Oxyethylene Methacrylate) (P(GMA)-b-P(OEM) or PGM-b-POEM)

oligo-oxyethylene methacrylate monomer (OEM, >99%, stabilized, Sigma-Aldrich, average molar mass=500 g mol$^{-1}$) was purified by passage through a basic alumina column.

The as-synthesized P(GMA) was used as a macroinitiator for the chain extension with OEM via ARGET ATRP. P(GMA) (0.5 g), OEM (2.10 g), $CuBr_2$ ($9.88 \times 10^{-4}$ g), PMDETA ($7.64 \times 10^{-3}$ g), and anisole (4 mL) were sealed in a round-bottom flask and sparged with argon for 30 minutes and subsequently heated to 60° C. Degassed tin(II) 2-ethylhexanoate (0.0179 g) was added to initiate the polymerization, and the reaction was allowed to proceed for 2 hours. The product was precipitated into water and dried for 48 h at room temperature and 48 hours at 120° C. before being brought into an argon-filled glovebox. The final polymer composition was determined by $^1$H NMR to have an overall molecular weight of 39,900 gmol$^{-1}$ with 72 wt % POEM.

Figure 9:
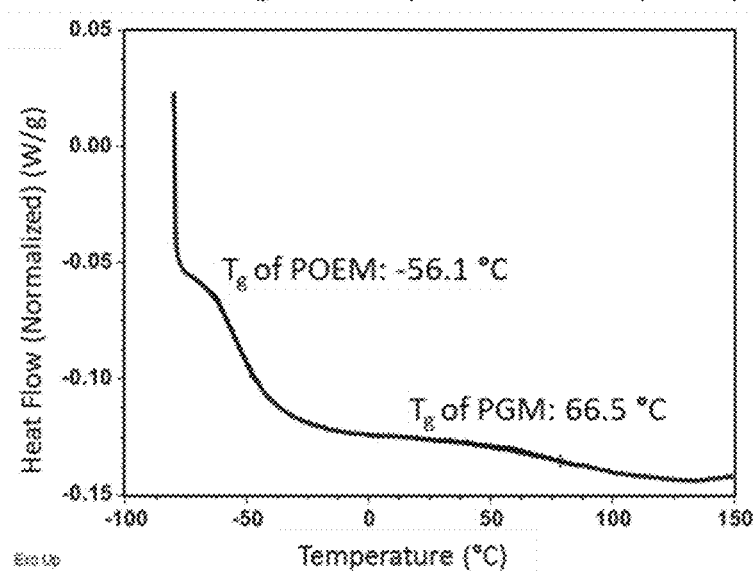
FIG. 9 shows thermal transitions in PGM-b-POEM as determined from DSC. Third heating trace is reported.

DSC (Discovery Series, TA Instruments) was used to determine the thermal properties of the as-prepared block copolymer (P(GMA)-b-P(OEM)) or PGM-b-POEM. In particular, the DSC was calibrated using an indium standard. PGM-b-POEM was loaded into an aluminum pan inside an argon-filled glovebox and hermetically sealed. Three heating and cooling cycles were performed at a rate of 5° C./min under nitrogen flow with a temperature range of −80-150° C. There were not significant changes between the second and third heating cycles, and the third cycle is shown in FIG. 9. The $T_g$s were determined as the midpoint of the inflection in the third heating. There were two distinct $T_g$s corresponding to the P(OEM) (−56.1° C.) and the P(GMA) (66.5° C.). The $T_g$ of the P(GMA) is lower than previously reported in the bulk P(GMA) because of the lower molecular weight in the synthesized block copolymer. One simple strategy to mitigate this lower $T_g$, would be to increase the molecular weight of the block copolymer.

Lithium Salt-Doping of the as-Prepared Block Copolymer (P(GMA)-b-P(OEM))

P(GMA)-b-P(OEM) and lithium triflate separately were dissolved in THF (degassed via 3 freeze-pump-thaw cycles) in an argon-filled glovebox. The desired amount of lithium triflate solution was added to the polymer solution such that the overall ratio of [EO]:[Li]=20:1. The solution then was dried under vacuum until all of the THF was removed; the salt-doped polymer was stored in an argon-filled glovebox.

Alternating Current Impedance Spectroscopy to Measure Conductivity of the Lithium Doped P(GMA)-b-P(OEM)

The lithium triflate-doped PGM-b-POEM was hot-pressed into disks under vacuum in an argon-filled glovebox. With a homemade test cell on a Linkam HFS91 CAP stage, a Princeton Applied Research PARSTAT 2273 frequency response analyzer was used to extract the ionic conductivity of the samples.

Figure 10:
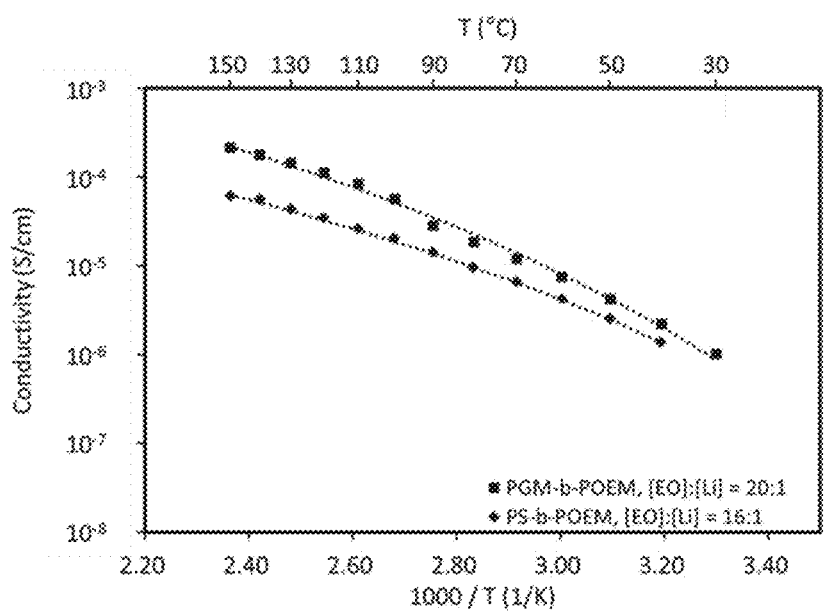
FIG. 10 shows conductivity (alternating current impedance spectroscopy) as a function of temperature of PGM-b-POEM (squares) and PS-b-POEM (diamonds).

First, the electrolytes were pre-annealed for 2 hours at 120° C., then cooled to 30° C. at 30° C. min$^{-1}$ and held for 30 minutes. Impedance measurements were taken under dynamic vacuum on heating from 30° C. to 150° C. and two measurements were taken at each temperature to ensure consistency. The average of the two measurements are reported herein, but deviations were within the size of the data point. The AC frequency range was 0.1-1 MHz, and the voltage amplitude was 10 mV. The resistance of the electrolyte was extracted from the high-frequency plateau in the real impedance data, and the conductivity was calculated as the sample thickness divided by the product of the sample area and the resistance. The conductivity of the as prepared lithium doped P(GMA)-b-P(OEM) was measured as a function of temperature as shown in FIG. 10.

The conductivity was maximized at $2 \times 10^{-4}$ S cm$^{-4}$S cm$^{-1}$ at 150° C. The dotted line was indicative of the fit to the Vogel-Fulcher-Tammann (VFT) equation (equation 1).

$$\sigma = \sigma_a e^{-\frac{B}{T-T_a}} \tag{1}$$

Comparison of the Bio-Based Electrolyte Material of the Present Invention, (P(GMA)-b-P(OEM) or PGM-b-POEM) with a Similar Non-Bio-Based Alternative (Polystyrene-b-P(OEM) or PS-b-POEM).

The bio-based electrolyte material of the present invention was compared with a similar non-bio-based alternatives (PS-b-POEM). PS-b-POEM was synthesized by ATRP. The polystyrene block was polymerized at 90° C. in a mixture of Cu(I)Br, PMDETA, styrene, and anisole, using EBiB as an initiator. Reaction proceeded for 14 h and was terminated by cooling with liquid nitrogen and exposing to air. The polystyrene block was purified with passage through a neutral alumina and precipitated two times into methanol. The polystyrene was used as a macroinitiator in an ATRP polymerization of OEM in a mixture of Cu(I)Br, PMDETA, OEM, and anisole at 90° C. The reaction proceeded for 4 h and was terminated by cooling with liquid nitrogen and exposing to air. The final polymer was passed through a neutral alumina column and precipitated into a mixture of equal volumes of diethyl ether and petroleum ether. The PS-b-POEM was dried at 120° C. for 48 h and stored in an argon-filled glovebox. Conductivities of the P(GMA)-b-POEM doped with lithium triflate at [EO]:[Li]=20:1 and of a PS-b-POEM doped with lithium triflate at [EO]:[Li]=16:1 are shown in FIG. 10. It should be noted that the bio-based electrolyte material has a higher conductivity despite the higher salt doping ratio.

The conductivities shown in FIG. 10 were fitted with VFT equation (1) and the VFT fitting parameters $\sigma_o$ and B are summarized below in Table 3. $\sigma_o$ is indicative of the effective charge carrier concentration and B is an effective activation energy, which is related to the segmental chain motion of the polymer. Thus, the higher conductivity is largely due to the bio-based polymer's higher effective charge carrier concentration (despite a lower lithium ion concentration), as the effective activation energy (B) is higher for the bio-based electrolyte.

TABLE 3

VFT fitting parameters of the bio-based and traditional electrolytes

| | $\sigma_o$ (S cm$^{-1}$) | B (K) |
| --- | --- | --- |
| P(GMA)-b-POEM | 0.052 | 1310 |
| PS-b-POEM | 0.0064 | 1130 |

Furthermore, it should be noted in FIG. 10, that by shifting the operating temperature from 90° C. (<$T_{g,PS}$) to 110° C. (<$T_{g,P(GMA)}$), conductivity increases by almost 300%.

REFERENCES (1) Laurichesse, S.; Avérous, L. Chemical modification of lignins: towards biobased polymers. Progress in Polymer Science 2014, 39 (7), 1266-1290.
(2) Sun, Z.; Fridrich, B.; de Santi, A.; Elangovan, S.; Barta, K. Bright side of lignin depolymerization: toward new platform chemicals. Chemical Reviews 2018, 118 (2), 614-678.
(3) Chung, H.; Washburn, N. R. Chemistry of lignin-based materials. Green Materials 2013, 1 (3), 137-160.
(4) Shuai, L.; Amiri, M. T.; Questell-Santiago, Y. M.; Héroguel, F.; Li, Y.; Kim, H.; Meilan, R.; Chapple, C.; Ralph, J.; Luterbacher, J. S. Formaldehyde stabilization facilitates lignin monomer production during biomass depolymerization. Science 2016, 354 (6310), 329-333.
(5) Shuai, L.; Saha, B. Towards high-yield lignin monomer production. Green Chemistry 2017, 19 (16), 3752-3758.
(6) Liu, W.; Jiang, H.; Yu, H. Thermochemical conversion of lignin to functional materials: a review and future directions. Green Chemistry 2015, 17 (11), 4888-4907.
(7) Wu, W.; Dutta, T.; Varman, A. M.; Eudes, A.; Manalansan, B.; Loqué, D.; Singh, S. Lignin valorization: two hybrid biochemical routes for the conversion of polymeric lignin into value-added chemicals. Scientific Reports 2017, 7 (1), 8420.
(8) Gall, D. L.; Ralph, J.; Donohue, T. J.; Noguera, D. R. Biochemical transformation of lignin for deriving valued commodities from lignocellulose. Current Opinion in Biotechnology 2017, 45, 120-126.
(9) Deuss, P. J.; Barta, K. From models to lignin: transition metal catalysis for selective bond cleavage reactions. Coordination Chemistry Reviews 2016, 306, 510-532.
(10) Ferrini, P.; Rinaldi, R. Catalytic biorefining of plant biomass to non-pyrolytic lignin bio-oil and carbohydrates through hydrogen transfer reactions. Angewandte Chemie (International ed.) 2014, 53 (33), 8634-8639.
(11) Deepa, A. K.; Dhepe, P. L. Lignin depolymerization into aromatic monomers over solid acid catalysts. ACS Catalysis 2015, 5 (1), 365-379.
(12) Song, Q.; Wang, F.; Xu, J. Hydrogenolysis of lignosulfonate into phenols over heterogeneous nickel catalysts. Chemical Communications 2012, 48 (56), 7019-7021.
(13) Choi, H. S.; Meier, D. Fast pyrolysis of Kraft lignin-vapor cracking over various fixed-bed catalysts. Journal of Analytical and Applied Pyrolysis 2013, 100, 207-212.
(14) Calvaruso, G.; Clough, M. T.; Rinaldi, R. Biphasic extraction of mechanocatalytically-depolymerized lignin from water-soluble wood and its catalytic downstream processing. Green Chemistry 2017, 19 (12), 2803-2811.
(15) van de Pas, D. J.; Torr, K. M. Biobased epoxy resins from deconstructed native softwood lignin. Biomacromolecules 2017, 18 (8), 2640-2648.
(16) Rouméas, L.; Billerach, G.; Aouf, C.; Dubreucq, É.; Fulcrand, H. Furylated flavonoids: fully biobased building blocks produced by condensed tannins depolymerization. ACS Sustainable Chemistry & Engineering 2018, 6 (1), 1112-1120.
(17) Holmberg, A. L.; Stanzione, J. F.; Wool, R. P.; Epps, T. H., III. A facile method for generating designer block copolymers from functionalized lignin model compounds. ACS Sustainable Chemistry & Engineering 2014, 2 (4), 569-573.
(18) Wang, S.; Bassett, A. W.; Wieber, G. V.; Stanzione, J. F., III; Epps, T. H., III. Effect of methoxy substituent position on thermal properties and solvent resistance of lignin-inspired poly(dimethoxyphenyl methacrylate)s. ACS Macro Letters 2017, 6 (8), 802-807.
(19) Holmberg, A. L.; Nguyen, N. A.; Karavolias, M. G.; Reno, K. H.; Wool, R. P.; Epps, T. H., III. Softwood lignin-based methacrylate polymers with tunable thermal and viscoelastic properties. Macromolecules 2016, 49 (4), 1286-1295.
(20) Holmberg, A. L.; Reno, K. H.; Nguyen, N. A.; Wool, R. P.; Epps, T. H., III. Syringyl methacrylate, a hardwood lignin-based monomer for high-Tg polymeric materials. ACS Macro Letters 2016, 5 (5), 574-578.
(21) Stanzione, J. F., III; Giangiulio, P. A.; Sadler, J. M.; La Scala, J. J.; Wool, R. P. Lignin-based bio-oil mimic as biobased resin for composite applications. ACS Sustainable Chemistry & Engineering 2013, 1 (4), 419-426.
(22) Stanzione, J. F., III; Sadler, J. M.; La Scala, J. J.; Reno, K. H.; Wool, R. P. Vanillin-based resin for use in composite applications. Green Chemistry 2012, 14 (8), 2346-2352.
(23) Holmberg, A. L.; Reno, K. H.; Wool, R. P.; Epps, T. H., III. Biobased building blocks for the rational design of renewable block polymers. Soft Matter 2014, 10 (38), 7405-7424.
(24) Saito, T.; Brown, R. H.; Hunt, M. A.; Pickel, D. L.; Pickel, J. M.; Messman, J. M.; Baker, F. S.; Keller, M.; Naskar, A. K. Turning renewable resources into value-added polymer: development of lignin-based thermoplastic. Green Chemistry 2012, 14 (12), 3295-3303.

(25) Zhao, S.; Abu-Omar, M. M. Renewable thermoplastics based on lignin-derived polyphenols. Macromolecules 2017, 50 (9), 3573-3581.
(26) Gioia, C.; Lo Re, G.; Lawoko, M.; Berglund, L. Tunable thermosetting epoxies based on fractionated and well-characterized lignins. Journal of the American Chemical Society 2018, 140 (11), 4054-4061.
(27) Van den Bosch, S.; Schutyser, W.; Vanholme, R.; Driessen, T.; Koelewijn, S. F.; Renders, T.; De Meester, B.; Huijgen, W. J. J.; Dehaen, W.; Courtin, C. M.; Lagrain, B.; Boerjan, W.; Sels, B. F. Reductive lignocellulose fractionation into soluble lignin-derived phenolic monomers and dimers and processable carbohydrate pulps. Energy & Environmental Science 2015, 8 (6), 1748-1763.
(28) Creton, C. Pressure-sensitive adhesives: an introductory course. MRS Bulletin 2003, 28 (6), 434-439.
(29) Sinha, B. Pressure sensitive adhesives market by chemical composition (acrylic, rubber, ethylene vinyl acetate (EVA), silicone, polyurethane, and others), type (water based, hot melts, solvent based, and radiation based), application (labels, medical, graphics, tapes, and others) and end-use industry (automotive, packaging, building & construction, electronics, medical, consumer goods, and others)—global opportunity analysis and industry forecast, 2017-2023. https://www.alliedmarketresearch.com/pressure-sensitive-adhesives-market. (accessed Mar. 5, 2018).
(30) Peykova, Y.; Lebedeva, O. V.; Diethert, A.; Müller-Buschbaum, P.; Willenbacher, N. Adhesive properties of acrylate copolymers: Effect of the nature of the substrate and copolymer functionality. International Journal of Adhesion and Adhesives 2012, 34, 107-116.
(31) O'Connor, A. E.; Willenbacher, N. The effect of molecular weight and temperature on tack properties of model polyisobutylenes. International Journal of Adhesion and Adhesives 2004, 24 (4), 335-346.
(32) Tobing, S. D.; Klein, A. Molecular parameters and their relation to the adhesive performance of acrylic pressure-sensitive adhesives. Journal of Applied Polymer Science 2001, 79 (12), 2230-2244.
(33) Gotro, J. T.; Graessley, W. W. Model hydrocarbon polymers: rheological properties of linear polyisoprenes and hydrogenated polyisoprenes. Macromolecules 1984, 17 (12), 2767-2775.
(34) Roovers, J.; Toporowski, P. M. Characteristic ratio and plateau modulus of 1,2-polybutadiene. A comparison with other rubbers. Rubber Chemistry and Technology 1990, 63 (5), 734-746.
(35) Nakamura, Y.; Adachi, M.; Tachibana, Y.; Sakai, Y.; Nakano, S.; Fujii, S.; Sasaki, M.; Urahama, Y. Tack and viscoelastic properties of an acrylic block copolymer/tackifier system. International Journal of Adhesion and Adhesives 2009, 29 (8), 806-811.
(36) Tong, J. D.; Jerôme, R. Synthesis of poly(methyl methacrylate)-b-poly(n-butyl acrylate)-b-poly(methyl methacrylate) triblocks and their potential as thermoplastic elastomers. Polymer 2000, 41 (7), 2499-2510.
(37) Vendamme, R.; Schüwer, N.; Eevers, W. Recent synthetic approaches and emerging bio-inspired strategies for the development of sustainable pressure-sensitive adhesives derived from renewable building blocks. Journal of Applied Polymer Science 2014, 131 (17), 40669.
(38) Nasiri, M.; Reineke, T. M. Sustainable glucose-based block copolymers exhibit elastomeric and adhesive behavior. Polymer Chemistry 2016, 7 (33), 5233-5240.
(39) Gallagher, J. J.; Hillmyer, M. A.; Reineke, T. M. Acrylic triblock copolymers incorporating isosorbide for pressure sensitive adhesives. ACS Sustainable Chemistry & Engineering 2016, 4 (6), 3379-3387.
(40) Ye, Y.; Zhang, Y.; Fan, J.; Chang, J. Selective production of 4-ethylphenolics from lignin via mild hydrogenolysis. Bioresource Technology 2012, 118, 648-651.
(41) Barner-Kowollik, C.; Perrier, S. The future of reversible addition fragmentation chain transfer polymerization. Journal of Polymer Science Part A: Polymer Chemistry 2008, 46 (17), 5715-5723.
(42) Lee, S.; Lee, K.; Kim, Y.; Shin, J. Preparation and characterization of a renewable pressure-sensitive adhesive system derived from s-decalactone, 1-lactide, epoxidized soybean oil, and rosin ester. ACS Sustainable Chemistry & Engineering 2015, 3 (9), 2309-2320.
(43) Shin, J.; Martello, M. T.; Shrestha, M.; Wissinger, J. E.; Tolman, W. B.; Hillmyer, M. A. Pressure-sensitive adhesives from renewable triblock copolymers. Macromolecules 2011, 44 (1), 87-94.
(44) Ding, K.; John, A.; Shin, J.; Lee, Y.; Quinn, T.; Tolman, W. B.; Hillmyer, M. A. High-performance pressure-sensitive adhesives from renewable triblock copolymers. Biomacromolecules 2015, 16 (8), 2537-2539.
(45) Emerson, J. A.; Toolan, D. T. W.; Howse, J. R.; Furst, E. M.; Epps, T. H., III. Determination of solvent-polymer and polymer-polymer Flory-Huggins interaction parameters for poly(3-hexylthiophene) via solvent vapor swelling. Macromolecules 2013, 46 (16), 6533-6540.

What is claimed is:

1. An article comprising an adhesive composition deposited on a substrate, wherein the adhesive composition comprises a bio-based block copolymer comprising:
(i) at least one bio-based polymeric block comprising, in polymerized form, at least one polymerizable bio-based monomer having a structure corresponding to formula (II):

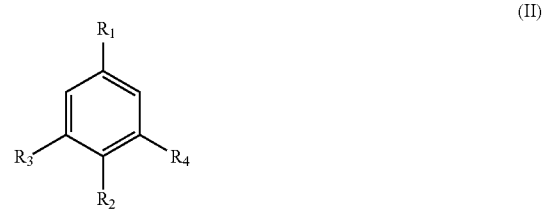

wherein $R_1$ is hydrogen, methyl, ethyl, n-propyl, i-propyl, propylene, a propanoate salt, a propanoate ester, an acetate salt, or an acetate ester,
wherein $R_2$ is a substituent comprised of at least one polymerizable functional group that is an ethylenically unsaturated functional group added via functionalization of a phenolic hydroxy (—OH) group,
wherein $R_3$ and $R_4$ are independently selected from hydrogen or methoxy,
wherein at least one of $R_1$, $R_3$ and $R_4$ is not hydrogen, and
wherein the ethylenically unsaturated functional group has been polymerized in the at least one bio-based polymeric block; and
(ii) a co-monomer-based polymeric block comprising, in polymerized form, at least one co-monomer other than the at least one bio-based monomers, wherein the at least one co-monomer comprises a butyl [meth]acrylate, wherein the bio-based block copolymer is a linear block copolymer.

2. The article of claim 1, wherein the adhesive composition is a pressure sensitive adhesive composition.

3. The article of claim 1 further comprising one or more additives selected from the group consisting of plasticizers, viscosity modifiers, photoluminescent agent, anti-counterfeit and UV-reactive additives, dyes/pigments, anti static materials, surfactants, and lubricants.

4. The article of claim 1, wherein the substrate comprises a polymeric film, a paper label, a tape backing, a graphic article, a plastic article, a metal article, a wound dressing, a protection film or tape, or a release liner.

5. The article of claim 1, wherein the at least one polymerizable functional group include methacrylate, acrylate, maleinate, maleate, fumarate, acrylamide, methacrylamide, vinyl, allyl, vinyl ester, or vinyl amide groups.

6. The article of claim 1, wherein the at least one polymerizable bio-based monomer comprises:
(a) a phenol [meth]acrylate selected from the group consisting of cresol [meth]acrylate, 4-ethylphenol [meth]acrylate, 4-propylphenol [meth]acrylate, 4-hydroxybenzaldehyde [meth]acrylate, and 3-(4-hydroxyphenol)propanoate [meth]acrylate;
(b) a monomethoxyphenol [meth]acrylate selected from the group consisting of guaiacol (monomethoxy-substituted phenol) [meth]acrylate, 4-ethylguaiacol [meth]acrylate, creosol [meth]acrylate, 4-propylguaiacol [meth acrylate, vanillin [meth]acrylate, and methyl homovaniliate [meth]acrylate (methyl 2-(4-hydroxy-3-methoxyphenyl)acetate [meth]acrylate);
(c) a dimethoxyphenol [meth]acrylate selected from the group consisting of syringol (dimethoxy-substituted phenol) [meth]acrylate, 4-methvisvringyilmethiacrylate, 4-ethylsyringyl[meth]acrylate, 4-n-propylsyringyl [meth]acrylate, 4-i-propylsyringyl[meth]acrylate, 4-propylenesyringyl[meth]acrylate, 4-formylsyringyl [meth]acrylate, 4-propanoatesyringyl[meth]acrylate salt, 4-propanoatesyringyl[meth]acrylate ester, 4-acetatesyringyl[meth]acrylate salt, and 4-acetatesyringyl [meth]acrylate ester; or
(d) combinations thereof.

7. The article of claim 1, wherein at least one of $R_3$, and $R_4$ is methoxy.

8. The article of claim 1, wherein the adhesive composition does not include a tackifier.

9. An article comprising an adhesive composition deposited on a substrate, wherein the adhesive composition comprises a bio-based block copolymer comprising:
(i) at least one bio-based polymeric block comprising, in polymerized form, at least one polymerizable bio-based monomer having a structure corresponding to formula (II):

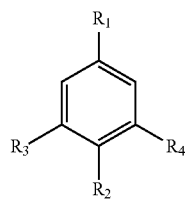

wherein $R_1$ is hydrogen, methyl, ethyl, n-propyl, i-propyl, propylene, formyl, a propanoate salt, a propanoate ester, an acetate salt, or an acetate ester, wherein $R_2$ is a substituent comprised of at least one polymerizable functional group that is an ethylenically unsaturated functional group added via functionalization of a phenolic hydroxy (—OH) group,
wherein $R_3$ and $R_4$ are independently selected from hydrogen or methoxy, and
wherein the ethylenically unsaturated functional group has been polymerized in the at least one bio-based polymeric block; and
(ii) a co-monomer-based polymeric block comprising, in polymerized form, at least one co-monomer other than the at least one bio-based monomers, wherein the at least one co-monomer comprises an alkyl [meth]acrylate, a diene, or an olefin, wherein the alkyl group is selected from the group consisting of methyl, ethyl, propyl and butyl, and
wherein the bio-based block copolymer is a bio-based triblock copolymer, having a midblock and two glassy end blocks, wherein the midblock is comprised of the alkyl [meth]acrylate in polymerized form and one or both of the glassy end blocks is or are comprised of the at least one bio-based monomer in polymerized form.

10. The article of claim 9, wherein $R_1$ is propyl and $R_3$ and $R_4$ are methoxy; and wherein the triblock bio-based copolymer is poly(4-propylsyringyl acrylate-b-butyl acrylate-b-4-propylsyringyl acrylate) having the following structure (V):

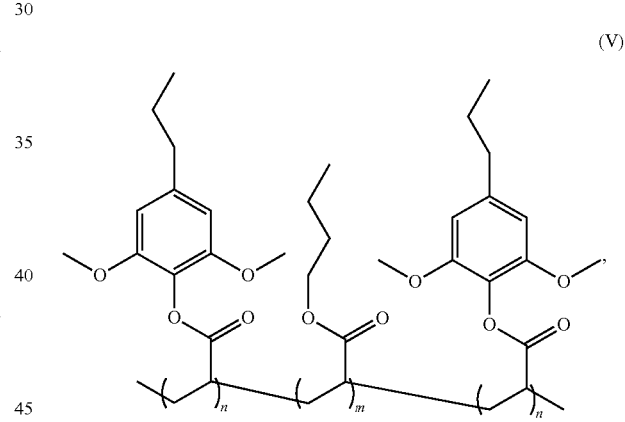

and
wherein n is in the range of 20-100; and m is in the range of 50-1000.

11. The article of claim 9, wherein the adhesive composition is a pressure sensitive adhesive composition.

12. The article of claim 9 further comprising one or more additives selected from the group consisting of plasticizers, viscosity modifiers, photoluminescent agent, anti-counterfeit and UV-reactive additives, dyes/pigments, anti-static materials, surfactants, and lubricants.

13. The article of claim 9, wherein the substrate comprises a polymeric film, a paper label, a tape backing, a graphic article, a plastic article, a metal article, a wound dressing, a protection film or tape, or a release liner.

14. The article of claim 9, wherein the at least one polymerizable functional group include methacrylate, acrylate, maleinate, maleate, fumarate, acrylamide, methacrylamide, vinyl, allyl, vinyl ester, or vinyl amide groups.

15. The article of claim 9, wherein the at least one polymerizable bio-based monomer comprises:

a phenol [meth]acrylate selected from the group consisting of cresol [meth]acrylate, 4-ethylphenol [meth]acrylate, 4-propylphenol [meth]acrylate, 4-hydroxybenzaldehyde [meth]acrylate, and 3-(4-hydroxyphenol) propanoate [meth]acrylate;

(ii) a monomethoxyphenol [meth]acrylate selected from the group consisting of guaiacol (monomethoxy-substituted phenol) [meth]acrylate, 4-ethylguaiacol [meth]acrylate, creosol [meth]acrylate, 4-propylguaiacol [meth]acrylate, vanillin [meth]acrylate, and methyl hornovanillate [meth]acrylate (methyl 2-(4-hydroxy-3-methoxyphenyl)acetate [meth]acrylate);

(iii) a dimethoxyphenol [meth]acrylate selected from the group consisting of syringol (dimethoxy-substituted phenol) [meth]acrylate, 4-methylsyringyl[meth]acrylate, 4-ethylsyringyl[meth]acrylate, 4-n-propylsyringyl [meth]acrylate, propylsyringyl[meth]acrylate, 4-propylenesyringyl[meth]acrylate, 4-formylsyringy[meth]acrylate, 4-propanoatesyringyl[meth]acrylate salt, 4-propanoatesyringyl[meth]acrylate ester, 4-acetatesyringyl[meth]acrylate salt, and 4-acetatesyringyl[meth] acrylate ester; or (iv) combinations thereof.

16. The article of claim 9, wherein at least one of R and $R_4$ is methoxy.

17. The article of claim 9, wherein the adhesive composition does not include a tackifier.

18. The article of claim 9, wherein at least one bio-based polymeric block comprises a bio-based copolymer block of 4-propylsyringol [meth]acrylate and 4-propylguaiacol [meth]acrylate.

19. An article comprising an adhesive composition deposited on a substrate, wherein the adhesive composition comprises a bio-based block copolymer comprising:

(i) at least one bio-based polymeric block comprising, in polymerized form, at least one polymerizable bio-based monomer having a structure corresponding to formula (II);

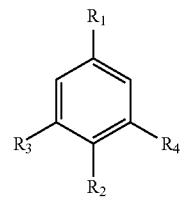

(II)

wherein $R_1$ is hydrogen, methyl, ethyl, n-propyl, i-propyl, propylene, a propanoate salt, a propanoate ester, an acetate salt, or an acetate ester, wherein $R_2$ is a substituent comprised of at least one polymerizable functional group that is an ethylenically unsaturated functional group added via functionalization of a phenolic hydroxy (—OH) group, wherein $R_3$ and $R_4$ are independently selected from hydrogen or methoxy, wherein at least one of $R_1$, $R_3$ and $R_4$ is not hydrogen, and wherein the ethylenically unsaturated functional group has been polymerized in the at least one bio-based polymeric block; and (ii) a co-monomer-based polymeric block comprising, in polymerized form, at least one co-monomer other than the at least one bio-based monomers, wherein the at least one co-monomer comprises a butyl [meth]acrylate, wherein at least one bio-based polymeric block comprises a bio-based copolymer block of 4-propylsyringol [meth]acrylate and 4-propylguaiacol [meth]acrylate.

* * * * *